United States Patent [19]

Murakami et al.

[11] Patent Number: 5,587,392

[45] Date of Patent: Dec. 24, 1996

[54] AZOLYL METHYL PHENYL DERIVATIVES HAVING AROMATASE INHIBITORY ACTIVITY

[75] Inventors: Kimihiro Murakami; Shuhei Ohnishi; Takashi Yano; Manabu Itoh, all of Tokyo, Japan

[73] Assignee: Mochida Pharmaceutical Co., Ltd., Tokyo, Japan

[21] Appl. No.: 453,054

[22] Filed: May 26, 1995

[30] Foreign Application Priority Data

May 27, 1994 [JP] Japan .................................. 6-115664

[51] Int. Cl.$^6$ ..................... A61K 31/41; C07D 403/12; C07D 403/10; C07D 247/18

[52] U.S. Cl. ..................... 514/359; 514/382; 548/260; 548/267.2; 548/267.4; 548/267.8; 548/268.6

[58] Field of Search ..................... 514/359, 383; 548/260, 267.2, 267.4, 267.8, 268.6

[56] References Cited

U.S. PATENT DOCUMENTS

| | | |
|---|---|---|
| 4,617,307 | 10/1986 | Browne . |
| 4,755,526 | 7/1988 | Hirsch et al. . |
| 4,916,144 | 4/1990 | Strehlke et al. . |
| 5,021,434 | 6/1991 | Strehlke et al. . |

FOREIGN PATENT DOCUMENTS

| | | |
|---|---|---|
| 293978 | 12/1988 | European Pat. Off. . |
| 337929 | 10/1989 | European Pat. Off. . |
| 600315 | 6/1994 | European Pat. Off. . |

OTHER PUBLICATIONS

English language abstract of EP-A-600315 (1994).
"Imidazole Antimycotics: Inhibitors of Steroid Aromatase" by J. Ian Mason et al, Biochemical Pharmacology, 34, 1087–1902, 1985.

Primary Examiner—Patricia L. Morris
Attorney, Agent, or Firm—Birch, Stewart, Kolasch & Birch, LLP

[57] ABSTRACT

Compounds exerting excellent aromatase inhibitory activity in vivo and in vitro with higher specificity and greater safety are provided together with the salts thereof. Using the same, there are also provided, prophylactic agents and/or therapeutical agents of estrogen-dependent diseases, contraceptive agents for females, and aromatase inhibitory agents for use in the form of reagents for human or animals. The compounds are of the formula (I), wherein $R^2$ is represented by the formula (II) or (III).

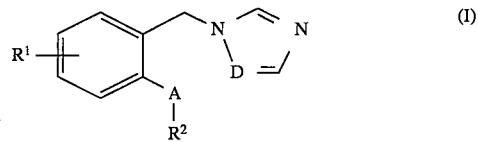

A: O, S, $CH_2$
D: CH, N

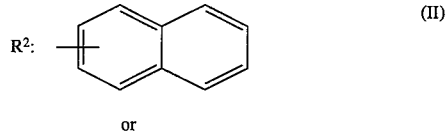

or

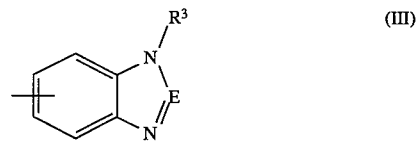

24 Claims, No Drawings

AZOLYL METHYL PHENYL DERIVATIVES HAVING AROMATASE INHIBITORY ACTIVITY

BACKGROUND OF THE INVENTION

1. Field of the Invention

The present invention relates to novel azolyl methyl phenyl derivatives, methods for producing the azolyl derivatives, aromatase inhibitory agents containing the azolyl derivatives, and pharmaceutical compositions containing the azolyl derivatives which compositions are useful as prophylactic and/or therapeutical agents of estrogen-dependent diseases.

2. Description of the Related Art

Aromatase is one of P-450 enzymes and catalyzes the aromatization of the A ring of the steroid skeleton in a series of the steroid biosynthetic pathway starting from the cleavage of the side chain of cholesterol; in other words, aromatase catalyzes the conversion from androstenedione to estrone and the conversion from testosterone to estradiol. Hence, aromatase is a rate limiting enzyme for the estrogen biosynthesis.

Therefore, a compound having an aromatase inhibitory activity should have an inhibitory activity on estrogen biosynthesis. Because it is anticipated that the compound lowers the blood estrogen level when administered to human or animals, it is believed that the compound may be applicable to estrogen dependent diseases which onset and exacerbation have relation with estrogen.

Such estrogen-dependent diseases include estrogen dependent-cancers (ex. breast cancer, ovarian cancer, endometrium cancer. etc.), endometriosis, uterine leiomyoma, benign breast diseases, mastopathy, premature labor, benign prostatic hyperplasia, prostate cancer, precocious puberty, gynecomastia, male infertility relating to oligospermia and cholelithiasis.

For therapeutical treatment of estrogen-dependent diseases, use has been made of a method for suppressing estrogen action in a target cell and a method for decreasing the estrogen level in blood. In a representative example of the former method, the administration of an estrogen antagonist such as tamoxifen has been in practice. However, clinically satisfactory effect cannot be brought about from such administration alone. In a representative example of the latter method, ovariectomy is generally performed so as to block estrogen generation via surgical treatment. Ovary is the main organ to produce estrogen. Such surgical treatment, however, causes a problem of damages on quality of life (abbreviated as "QOL" hereinafter) because a functional organ such as ovary essential for females is resected. Additionally, limitation and problems are remarked for its clinical application such that the decrease of blood estrogen level even by ovariectomy involves much difficulty in post menopausal patients; that the method is not applicable to male patients; and that the method is not applicable to estrogen produced by tumor cells themselves. On the other hand, greater attention has been focused on an internal treatment of estrogen-dependent diseases on the basis of the finding that an aromatase inhibitory agent as an agent for inhibiting estrogen synthesis brings about a lower estrogen state while maintaining QOL. Also, the treatment may be applicable to cases with no efficacy of any estrogen antagonist, post menopausal patients and male patients.

Aminoglutethimide (abbreviated to as "AG," hereinafter) having a weak aromatase inhibitory action, has been used for the treatment of some breast cancers. However, because AG has a higher potency to inhibit cleavage enzymes of cholesterol side chains and causes therefore the decrease of glucocorticoids and mineral corticoids essential for supporting life and hence supplemental therapy of these hormones is inevitable, the agent has not been applied in various fields of clinical practice.

It has been found that imidazole derivatives such as miconazole, clotrimazole and ketoconazole, which have been developed originally as antifungal agents and are now for clinical use, have aromatase inhibitory activities as well (see Biochemical Pharmacology, 34, 1087–1092, 1985). Nevertheless, these agents have not been used as therapeutical agents for treating estrogen-dependent diseases. The reason is considered that the agents do not show satisfactory specificity of the enzyme inhibition.

From the respect of their structures, aromatase inhibitory agents published in reports are grouped in steroidal agents and non-steroidal agents. Steroidal aromatase inhibitory agents include testolactone and 4-hydroxyandrostenedione, but testolactone never exerts sufficient therapeutical efficacy. These agents are poorly absorbed when administered orally, and will be also accompanied by side effects specific to steroids, so that the agents are not clinically satisfactory.

Non-steroidal aromatase inhibitory agents will now be described below in the following reports. Japanese Patent Laid-open No. Sho 61-12671 discloses N-substituted imidazoles and triazole compounds, having weak aromatase inhibitory action, but does not describe their enzyme specificity. Japanese Patent Laid-open No. Sho 61-12688 describes substituted bicyclo compounds. It is reported that CGS 16949A, one of these compounds, inhibits the biosynthesis of aldosterone, so that has no satisfactory enzyme specificity. Japanese Patent Laid-open No. Sho 63-316775 describes benzotriazole derivatives, but with no description of the enzyme specificity of these compounds. Their enzyme specificity is insufficient in a practical sense. Japanese Patent Laid-open No. Hei 1-290663 describes an N-substituted imidazole, but with no description of the activity in vivo or with no disclosure of pharmacological data concerning the specificity. However, the activity of benzyloxy-substituted imidazoles is practically lower in vivo. In other words, these prior art references do not encompass the disclosure of aromatase inhibitory activity in vivo; otherwise, the references simply disclose that their actions are weak with no satisfactory enzyme specificity. Therefore, it is not clear whether or not these compounds are clinically applicable.

SUMMARY OF THE INVENTION

It is the object of the present invention to overcome at least one of the problems in the prior art as described above. The development of a pharmaceutical agent with satisfactory actions in living organisms is now demanded, which has a higher enzyme specificity, specifically inhibiting only aromatase with no requirement of supplementing adrenocorticosteroid hormones and the like. In other words, a highly safe pharmaceutical agent with less side effects is now needed, which ensures the lowering of the estrogen level in humans with no effect on the synthesis of other steroid hormones in gonads and adrenal grands or with no effect on the drug metabolism involving cytochrome P-450 in liver. The object of the present invention resides in providing highly potent aromatase inhibitory agents with higher enzyme specificity, in providing aromatase inhibitory agents being capable of exerting satisfactory aromatase inhibitory action in human or animals and having higher enzyme specificity, in providing highly safe agents with less side effects for prophylactic and/or therapeutical treatment of estrogen-dependent diseases, in providing azolyl methyl phenyl derivatives useful for such utility and methods for producing the azolyl derivatives, and, in providing at least one thereof.

The present inventors have made intensive investigations so as to obtain a useful and highly safe non-steroidal inhibitory agent, which selectively inhibits aromatase alone among a great number of P-450 enzymes involved in steroid biosynthesis and has higher specificity in animals. Consequently, the inventors have found that specific azolyl methyl phenyl derivatives and the salts thereof have highly potent and selective activity of inhibiting aromatase. Thus, the present invention has been achieved.

A first aspect of the present invention is novel azolyl methyl phenyl derivatives represented by the following formula (I):

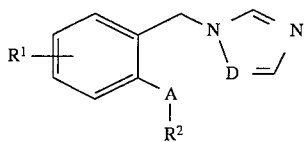

[wherein A represents methylene group, oxygen atom or sulfur atom; D represents nitrogen atom or methine group; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; $R^2$ represents an atomic group represented by formula (II);

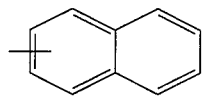

or formula (III);

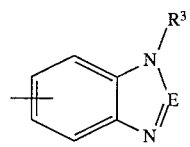

(wherein E represents nitrogen atom or methine group; and $R^3$ represents hydrogen atom or $C_1$ to $C_4$ alkyl group linear or branched)],
or the salts thereof.

Preferable combinations of the substituents in the compounds represented by the formula (I) are shown hereinbelow, but the present invention is not limited to these combinations.

For a combination of A, $R^1$ and $R^2$, A is preferably oxygen atom; the substituting position of $R^1$ is preferably at position 4; and $R^2$ is preferably an atomic group represented by the formula (III) and bound to position 6.

In addition to the combination, D is preferably nitrogen atom.

Furthermore, E is preferably nitrogen atom while $R^3$ is preferably methyl group.

Still furthermore, $R^1$ is halogen atom, cyano group or nitro group, more preferably.

Also, $R^1$ is vinyl group or ethynyl group, more preferably.

Most preferable compound in accordance with the present invention is a compound represented by the following formula (IV);

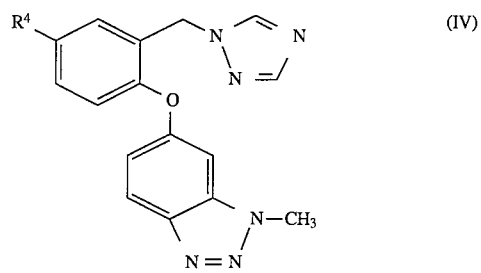

(wherein $R^4$ represents halogen atom, cyano group, nitro group, vinyl group or ethynyl group),
or the salts thereof.

A second aspect of the present invention is methods for producing said derivatives (Methods 1 to 3).

Method 1

Method for producing compounds represented by the following formula (I);

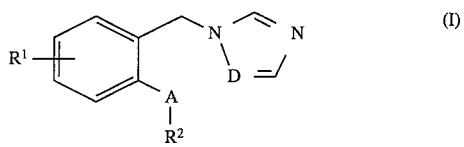

(wherein A, D, $R^1$, $R^2$ and, E and $R^3$ in the $R^2$ definition are as described above)
or the salts thereof, comprising reacting a benzyl halide derivative or a benzyl alcohol derivative, represented by the following formula (IX);

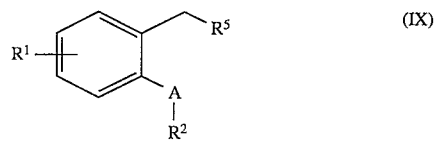

(wherein A represents methylene group, oxygen atom or sulfur atom; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; $R^2$ and, E and $R^3$ in the $R^2$ definition are the same as described in the formula (I);

and $R^5$ represents halogen atom or a protected or unprotected hydroxyl group)
or the salts thereof, with an azole compound represented by the following formula (X);

(wherein D represents nitrogen atom or methine group).

Method 2

Method for producing compounds represented by the following formula (I)-b;

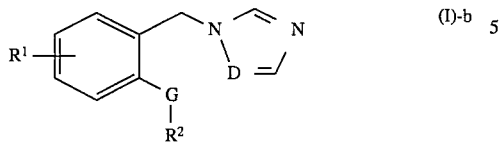
(I)-b (wherein G, D, R¹, R² and, E and R³ in the R² definition are as described above.)
or the salts thereof, comprising reacting a benzyl halide derivative or a benzyl alcohol derivative, represented by the following formula (VII);

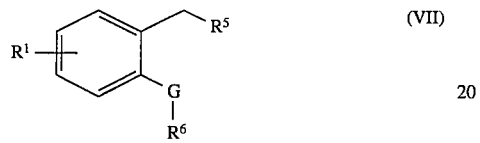
(VII)

[wherein G represents oxygen atom or sulfur atom; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; $R^5$ represents halogen atom or a protected or unprotected hydroxyl group; and $R^6$ is an atomic group represented by the following formula (II);

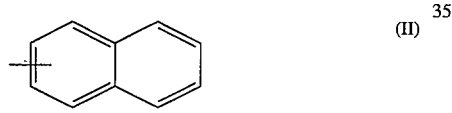
(II)

or the following formula (XI);

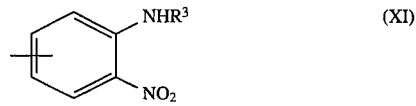
(XI)

(wherein $R^3$ represents hydrogen atom or $C_1$ to $C_4$ alkyl group linear or branched)],
or the salts thereof, with an azole compound represented by the following formula (X);

(X)

(wherein D represents the same as described above), thereby producing an azolyl methyl phenyl derivative represented by the following formula (VIII);

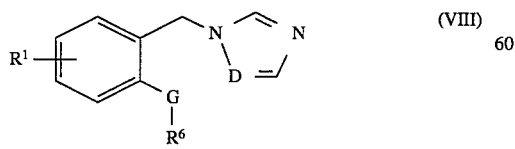
(VIII)

[wherein G represents oxygen atom or sulfur atom; D represents nitrogen atom or methine group; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; and $R^6$ represents an atomic group represented by the following formula (II);

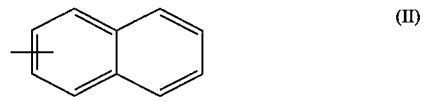
(II)

or by the following formula (XI);

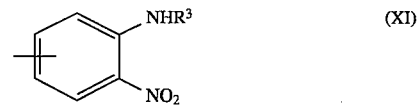
(XI)

(wherein $R^3$ represents the same as described above)],
or the salts thereof, followed by reduction and subsequent cyclization reaction, if necessary.

Method 3

Method for producing compounds represented by the following formula (I)-b;

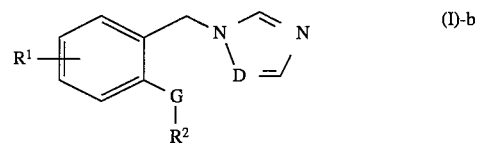
(I)-b (wherein G, D, R¹, R² and, E and R³ in the R² definition are as described above.)
or the salts thereof, comprising reacting an azolyl methyl phenol or an azolyl methyl thiophenol derivative, represented by the following formula (VI);

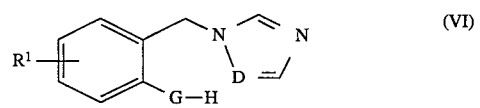
(VI)

(wherein G represents oxygen atom or sulfur atom; D represents nitrogen atom or methine group; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom),
or the salts thereof, with a aryl halide represented by formula $R^6X$, [wherein X represents halogen atom and $R^6$ represents an atomic group represented by the following formula (II);

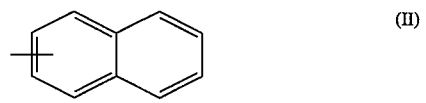
(II)

or by the following formula (XI);

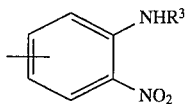

(wherein $R^3$ represents the same as described above)], thereby producing an azolyl methyl phenyl derivative represented by the following formula (VIII);

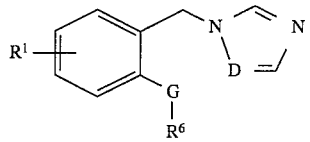

(wherein G, D, $R^1$, $R^6$ and $R^3$ described in the $R^6$ definition are the same as described above)

or the salts thereof, followed by reduction and subsequent cyclization reaction, if necessary.

A third aspect of the present invention is prophylactic agents and/or therapeutical agents of estrogen-dependent diseases, containing at least one of the compounds represented by the formula (I) or the salts thereof as the active component.

For a combination of A, $R^1$ and $R^2$, A is preferably oxygen atom; the substituting position of $R^1$ is preferably at position 4; and $R^2$ is preferably an atomic group represented by the formula (III) and bound to position 6.

In addition to the combination, D is preferably nitrogen atom.

Furthermore, E is preferably nitrogen atom while $R^3$ is preferably methyl group.

Still furthermore, $R^1$ is halogen atom, cyano group or nitro group, more preferably.

Also, $R^1$ is vinyl group or ethynyl group, more preferably.

Most preferable compound useful as the prophylactic agents and/or therapeutical agents in accordance with the present invention is the compound represented by the following formula (IV) (wherein $R^4$ is the same as described above) or the salts thereof.

A fourth aspect of the present invention is aromatase inhibitory agents containing at least one of the compounds represented by the formula (I) or the salts thereof as the active component.

In the formula, preferable examples of A, D, $R^1$, $R^2$ and, E and $R^3$ in the $R^2$ definition as well as most preferable such compound are the same as in the third aspect of the present invention described above.

The present invention will now be explained in details.

The compounds of the present invention are represented by the above formula (I). In the formula, A represents methylene group, oxygen atom or sulfur atom, G represents A excluded methylene group, preferably oxygen atom; D s represents nitrogen atom or methine group, preferably nitrogen atom; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom, and preferably, $R^1$ is chlorine atom, bromine atom fluorine atom, iodine atom, cyano group, nitro group, methoxy group, trifluoromethoxy group, trifluoromethyl group, ethoxycarbonyl group, carboxyl group, acetyl group, formyl group or hydrogen atom; more preferably, $R^1$ is chlorine atom, bromine atom, iodine atom, cyano group, nitro group, vinyl group or ethynyl group, and the substituting position thereof is preferably at position 4 or 5, more preferably at position 4.

$R^2$ represents an atomic group represented by the formula (II) or formula (III), preferably an atomic group represented by the formula (III). The substituting position of the atomic group represented by the formula (III) is preferably at position 5 or 6, more preferably at position 6. In the formula, E represents nitrogen atom or methine group; $R^3$ represents hydrogen atom or $C_1$ to $C_4$ alkyl group linear or branched, preferably methyl group or ethyl group.

The above substituted position will be explained. The substituted positions by $R^1$ in the formula (I) are numbered position 1 to the carbon atom bound to A, subsequently, the following carbon atoms from position 1 are numbered, for example position 3, position 4, position 5 or position 6. Formula (II) is naphthyl group, so that the substituted positions are represented for position α or position β. The substituted positions of formula (III) are numbered position 1 to the nitrogen atom bound to $R^3$, then, for example position 4, position 5, position 6 or position 7, subsequently.

The compounds of the present invention can form salts with an inorganic acid or an organic acid. Examples of these salts include salts with inorganic acids, such as hydrochloride, sulfate, nitrate, etc., salts with organic acids such as acetate, oxalate, p-toluenesulfonate, methanesulfonate, etc. These salts can be produced according to a known method, namely a process comprising mixing together equimolar amounts of one of the compounds of the present invention and a desirable acid in solution and recovering the desirable salt by filtration or solvent evaporation.

Most preferable compound of the present invention is a compound represented by the following formula (IV);

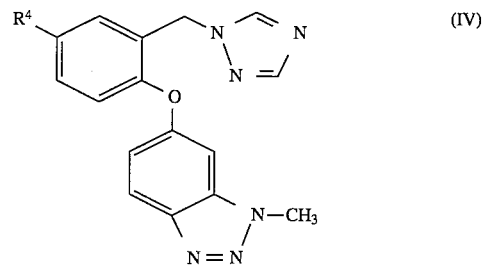

(wherein $R^4$ represents the same as described above), or the salts thereof.

More specifically, the compound is 6-[4-chloro-2-(1H-1,2,4-triazol-1-ylmethyl)phenoxy]-1-methyl-1H-benzotriazole (Example 41), 6-[4-bromo-2-(1H-1,2,4-triazol-1-ylmethyl)phenoxy]-1-methyl-1H-benzotriazole (Example 43), 1-methyl-6-[4-nitro-2-(1H-1,2,4-triazol-1-ylmethyl)phenoxy]-1H-benzotriazole (Example 50), or 4-[6-(1-methyl-1H-benzotriazoyloxy)]-3-(1H-1,2,4-triazol-1-ylmethyl)benzonitrile (Example 52).

The compounds represented by the formula (I) in accordance with the present invention can be produced by the processes shown in the following reaction scheme. In the following reaction scheme and the description, a compound represented by the formula (V);

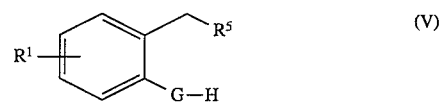

(wherein G represents oxygen atom or sulfur atom; and $R^5$ represents halogen atom or a protected or unprotected hydroxyl group), compounds individually represented by formulas (I), (I)-b, (II), (III), (VI), (VII), (VIII), (IX), (X), (XI), (XI), (XII), (XIII), (XIV), (XV) and formula (R⁶X), as well as $R^1$, $R^2$, $R^3$, $R^5$, $R^6$, A, D, E, G and X in the formulas, are the same as described above. Formula (I)-b is included formula (I).

Azolyl methyl phenyl derivatives represented by the formula (I) as the compounds of the present invention and the salts thereof may be synthesized, by reacting a compound represented by the formula (V) which can be readily produced from a compound known in references or commercially available, or a derivative represented by the formula (VII) or a derivative represented by the formula (IX) derived from the compound represented by the formula (VII) or the intermediate compound represented by the formula (XII), or the salts thereof, with a commercially available azole compound represented by the formula (X).

Synthesis of a derivative having a diaryl ether or a diaryl thioether bond as one of the essential skeletons of the compounds represented by the formula (I) in accordance with the present invention, is as follows; a compound represented by the formula (V) which can be readily produced from a compound known in references or commercially available or a compound represented by the formula (VI) which is derived from a compound represented by the formula (V), together with a aryl halide derivative represented by R⁶X is subjected to Ullmann reaction shown below in the reaction scheme; otherwise, such compound is subjected to a reaction to form an ether or thioether bond, which reaction is based on the characteristic properties of fluorine. Synthesis of an intermediate compound represented by formula (XII), is as follows; the intermediate compound can be derived from a compound represented by the formula (XIII) which can be readily produced from a compound known in references or commercially available. The reaction scheme of the present invention and the intermediate compounds represented by formula (XII) are schematically shown as follows.

Reaction Scheme

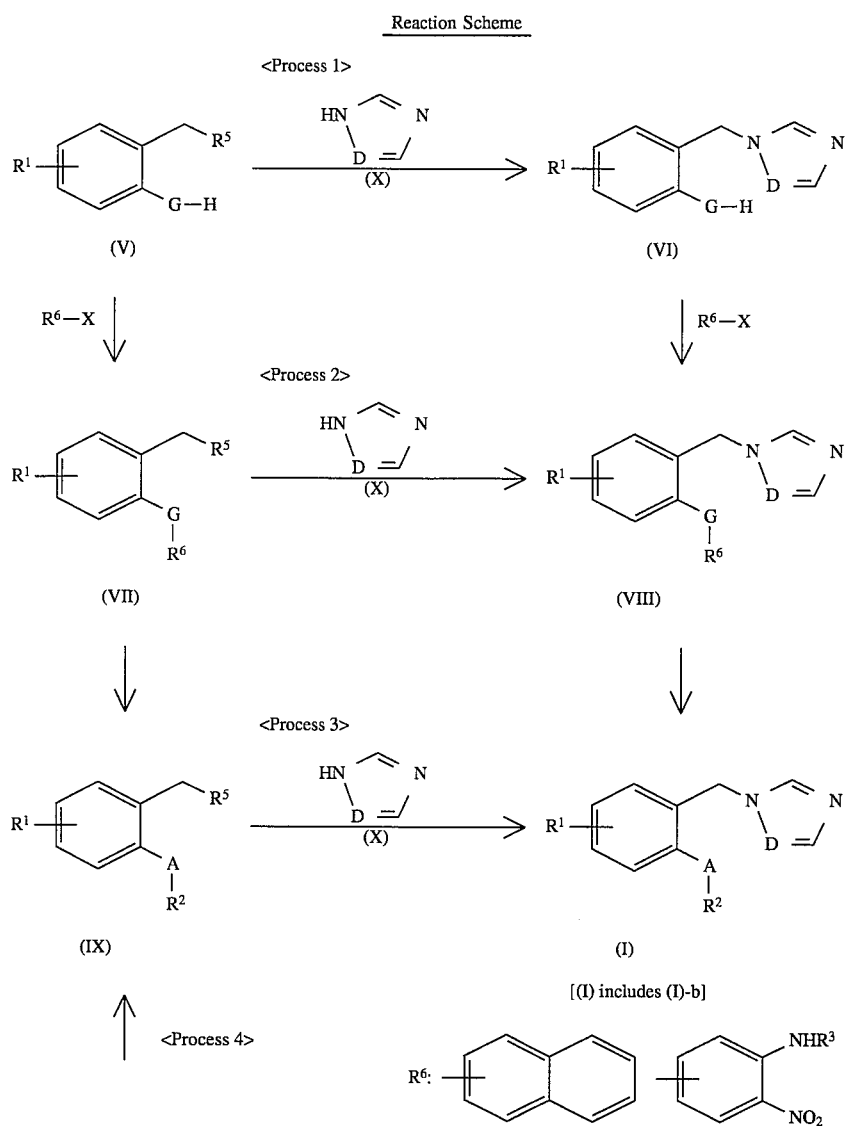

-continued
Reaction Scheme

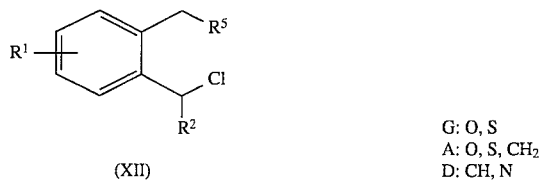

(XII)

G: O, S
A: O, S, CH$_2$
D: CH, N

Reaction Scheme to produce the intermediate compound represented by formula (XII)

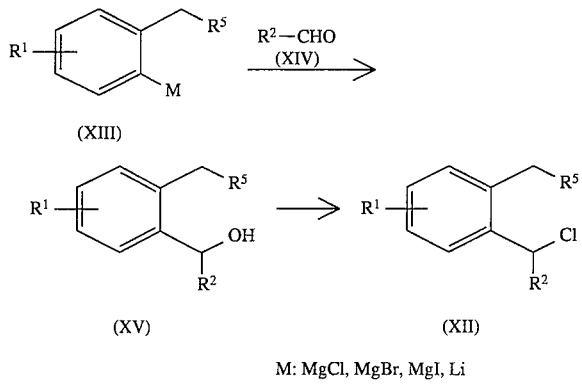

M: MgCl, MgBr, MgI, Li

The processes will now be described in details hereinbelow.

Process 1

1) Process of producing azolyl methyl phenol or azolyl methyl thiophenol compounds, represented by formula (VI)

By reacting together starting materials, i.e., a compound represented by the formula (V) and a compound represented by the formula (X), a compound represented by the formula (VI) can be produced. The reaction can proceed as follows, when $R^5$ is halogen atom in the compound represented by the formula (V). Using as a base an inorganic base such as potassium carbonate, cesium carbonate, calcium carbonate, etc. or an organic base such as triethylamine, pyridine, N,N-dialkylaniline, etc., preferably cesium carbonate as a base, and using as a solvent a polar solvent such as acetonitrile, dimethylformamide (DMF), etc., or a halogenated hydrocarbon solvent represented illustratively by chloroform, methylene chloride, etc., an ether solvent illustratively represented by ether, tetrahydrofuran (THF), etc., preferably using as a solvent acetonitrile, a halgenomethyl derivative reacts with an azole such as 1,2,4-triazole or imidazole at a temperature from room temperature to a temperature for the reflux of the reaction mixture under heating, preferably at a temperature under reflux conditions, for a time period enough for the reaction, specifically for 10 minutes to 3 hours.

In a suitable solvent with a higher boiling point such as decalin, dimethyl sulfoxide (DMSO), 1,2-dimethoxyethane (DME), dibutyl ether, DMF or 1,3-dimethyl-2-imidazolidone (DMI) or with no use of any solvent, preferably with no use of any solvent, at 120° to 200° C., preferably at 150° to 160° C., for a period enough for the reaction, specifically for 10 minutes to 3 hours, a compound represented by the formula (V) with $R^5$ being hydroxyl group reacts with 1,2,4-triazole or imidazole to directly introduce the azole group.

Among the starting materials, a compound represented by the formula (V) with $R^5$ being halogen atom can be produced by the following process.

Using a suitable halogenating agent such as chlorine gas, bromine, copper(II) bromide, N-bromosuccinimide (NBS), N-chlorosuccinimide (NCS), trihalogenomethane sulfonyl halogenide and trichlorobromomethane in the presence or absence of light or peroxide such as benzoyl peroxide (BPO), preferably using NBS in the presence of BPO, o-cresol or o-thiocresol which may or may not be substituted (corresponding to a compound of the formula (V) wherein $R^5$ is hydrogen atom) is converted into a halogenomethyl derivative, in a halogenated hydrocarbon solvent such as carbon tetrachloride, chloroform, methylene chloride, etc., an aromatic hydrocarbon non polar solvent such as benzene, toluene, etc., acetic acid or carbon disulfide, preferably in a solvent carbon tetrachloride, at a temperature from room temperature to a temperature for the reflux of the reaction mixture under heating, preferably at a temperature under reflux conditions for a period enough for the reaction, specifically for 1 hour to 5 hours.

Using a hydrogen halide such as hydrogen bromide, hydrogen chloride, etc., a halogenated phosphorus reagent such as phosphorus trichloride, phosphorus tribromide, phosphorus pentachloride, phosphorus pentabromide or phosphorus oxychloride, etc., a thionyl halide reagent such as thionyl chloride or thionyl bromide, a phosphonate triester reagent or a phosphine compound, such as (PhO)$_3$P-Br$_2$, Ph$_3$P-CCl$_4$ or Ph$_3$P-Br$_2$, a compound represented by the formula (V) with $R^5$ being hydroxyl group is converted into a halogenomethyl derivative with $R^5$ being halogen atom, preferably using a thionyl halide at an ice-cool temperature for the reflux of the reaction mixture under heating, at preferably an ice-cool temperature to room temperature for a period enough for the reaction, specifically for 5 minutes to 2 hours.

2) Process of producing diaryl ether or diaryl thioether compounds, represented by the formula (VIII) or the formula (I)-b A diaryl ether or diaryl thioether compound represented by the formula (VIII) can be produced generally by reacting the compound of the formula (VI), produced as described above, with an aryl halide represented by the formula $R^6X$. Using an inorganic base such as potassium hydroxide, potassium carbonate, etc. or an alkali metal reagent such as sodium alkoxide, sodium hydride, etc., the reaction of a compound represented by the formula (VI) with an aryl halide represented by the formula $R^6X$ may progress in the presence of copper powder or iron powder, preferably in the presence of copper powder. In this reaction, iodide or bromide is used as such aryl halide, but the reaction may readily proceed if the aromatic ring of a chloride is activated.

i) Provided that $R^6$ of the formula (VIII) (or $R^2$ of the formula (I)-b) is naphthalene ring, a compound represented by the formula (VI) is modified into phenoxide or thiophenoxide, using an inorganic base such as potassium hydroxide, potassium carbonate, etc. or an alkali metal reagent such as sodium alkoxide, sodium hydride, etc., preferably using potassium hydroxide or sodium methoxide. Then, the reaction of the resulting phenoxide or thiophenoxide with bromonaphthalene proceeds under heating in a suitable solvent with a higher boiling point such as DMF, DMSO, DME, dibutyl ether, xylene, decalin, or DMI, preferably in DMI at 100° to 200° C., preferably at 120° to 150° C. to yield a phenoxynaphthalene derivative or a thiophenoxynaphthalene derivative, represented by the formula (VIII) or the formula (I).

ii) For the synthesis of a compound of the formula (I)-b, having a benzimidazole ring or a benzotriazole ring in $R^2$, the synthesis may proceed by way of a compound represented by the formula (VIII), using a compound having an atomic group represented by the formula (XI) as $R^6$ of the formula $R^6X$.

Using the solvents, preferably DMI shown above in the item (i), a compound represented by the formula (VI) is heated along with a compound of the formula $R^6X$ having an atomic group represented by the formula (XI) in the presence of copper powder at 100° to 200° C., preferably at 120° to 150° C. for Ullmann reaction, to synthesize a compound represented by the formula (VIII).

iii) Alternatively, the following synthetic process may be adopted, provided that X is fluorine atom in the compound of the formula $R^6X$. A compound of the formula (VIII) may be synthesized by heating and reacting together a compound of the formula (VI) and a compound of the formula $R^6X$ having an atomic group represented by the formula (XI) with the provision of X being fluorine atom, i.e., a fluoronitroaniline derivative, in a solvent such as an inactive ether solvent such as dioxane, THF, DME, etc., or a polar solvent such as DMSO, DMF, and DMI, preferably in a solvent DMF, using as a base an inorganic base such as potassium hydroxide and potassium carbonate, an alkali metal reagent such as n-butyl lithium (n-BuLi), sodium alkoxide, sodium hydride, etc., preferably using as a base potassium carbonate, at room temperature to 200° C., preferably at 70° to 120° C. The process may proceed under mild reaction conditions, if the fluorobenzene derivative is readily available, and additionally, the process does not require any metal catalyst, so that the process is highly practical.

3) Process of producing a compound represented by the formula (I)-b

The compound represented by the formula (VIII) thus produced can be modified into a compound of the formula (I)-b as follows.

Via the reduction with zinc in an acetic acid solvent or via the reduction with stannic chloride or tin powder in hydrochloric acid or via hydrogenation under the presence of Raney-nickel or a palladium catalyst in such a solvent as alcohol, preferably via the reduction with zinc in an acetic acid solvent at −20° to 100° C., preferably under ice cooling to room temperature, the nitro group of a compound of the formula (VIII) is modified into an amino group. Through the reaction with sodium nitrite in the presence of a suitable mineral acid such as dilute sulfuric acid or dilute hydrochloric acid at −20° to 100° C., preferably under ice cooling to room temperature, the resulting diamino derivative is further modified into a benzotriazole derivative represented by the formula (I)-b, by way of a diazo compound. Alternatively, the diamino derivative described above is modified into a benzimidazole derivative of the formula (I)-b by the reflux of the diamino derivative under heating in formic acid or by using a suitable reagent such as triethyl orthoformate.

Process 2

According to the method described in Process 1-2), a compound of the formula (V) as a starting material reacts with an aryl halide represented by the formula $R^6X$ to produce a diaryl ether or a diaryl thioether, represented by the formula (VII). For the reaction, $R^5$ is preferably hydroxyl group.

When a naphthalene ring is introduced as $R^6$, a compound of the formula (V) is converted to phenoxide or thiophenoxide, using potassium hydroxide, sodium methoxide, etc, by the same method as in Process 1, namely Ullmann reaction using a halogenated aryl represented by the formula $R^6X$ and copper as a catalyst.

When an atomic group of the formula (XI) is introduced as $R^6$, the compound of the formula (V) is converted to a compound of the formula (VII), by Ullmann reaction or by a reaction by means of a fluorobenzene derivative.

Then, a compound of the formula (VII) reacts with an azole compound of the formula (X) following the process described in Process 1-1) to synthesize a compound of the formula (VIII). Herein, the reaction conditions are the same as described in Process 1-1).

Thus, a compound of the formula (I)-b with $R^2$ being naphthyl group can be produced, provided that $R^6$ is naphthyl group ($R^2=R^6$). Also, when $R^2$ is benzotriazole or benzimidazole in the compound of the formula (I)-b, the nitro group in $R^6$ of the compound of the formula (I)-b is converted into amino group according to the process described in Process 1-3), namely the reduction with zinc in acetic acid. The obtained diamino compound is converted to benzotriazole derivative via diazo compound using sodium nitrite with diluted sulfuric acid or diluted hydrochloric acid. Also the diamino compound described above is modified into a benzimidazole derivative represented by the formula (I), via reflux under heating in formic acid.

Process 3

A compound represented by the formula (VII) produced by the process described in Process 2 is modified into a compound of the formula (IX), provided that $R^6$ in the compound of the formula (VII) is an atomic group represented by the formula (XI). As a preferable, specific example thereof, a compound of the formula (VII) is modified into a diamino compound via the reduction with zinc in acetic acid, which is then modified into a benzotriazole compound of the formula (IX) by way of a diazo compound, via the action of sodium nitrite using dilute sulfuric acid or dilute hydrochloric acid. Also, with reflux under heating in formic acid, the diamino compound is modified into a benzimidazole derivative of the formula (IX). Provided that $R^6$ is naphthyl group, a compound represented by the formula (VII) is the same as the compound represented by the formula (IX).

According to the process described in Process 1-1), the compound represented by the formula (IX) reacts with an azole compound represented by the formula (X), for the synthesis of a compound of the formula (I). Herein, the reaction conditions are the same as described in Process 1-1).

Process 4

1) Process of producing diarylhalomethane intermediate compounds, represented by formula (XII)

A compound represented by the formula (XV) can be produced from the reaction of organometallic compound represented by the formula (XIII) with a compound represented by the formula (XIV). An organometallic compound represented by the formula (XII) can be prepared below.

The bromotoluene derivatives as starting materials can be converted to aldehyde intermediates using as oxidizing reagent such as manganese dioxide, chromic acid, lead tetraacetate, preferably chromic acid oxidation in the presence of acetic anhydride-sulfric acid. Aldehyde intermediates is reduced with metal hydride compound of boron, aluminum, silicon, tin, preferably sodium borohydride to hydroxymethyl intermediates.

Hydroxy group of hydroxymethyl intermediates is protected with appropriate protecting group according to "Protective groups in organic synthesis", 2nd ed 1991, T. W. Greene and P. G. M. Wutz, John Wiley and Sons, Inc, preferably silyl group. Protected hydroxymethyl intermediates can be converted to organo-magnesium compound using magnesium metal, or oranolithium compound using lithium metal, alkyl lithium, lithium amide, preferably n-butyl lithium.

Diarylmethanol intermediate represented by formula (XV) can be synthesized from prepared organometallic compound represented by formula (XIII), preferably Grignard reagent and arylaldehyde by formula (XIV) using as a solvent an inactive ether solvent such as ether, dioxane, THF, DME, preferably using ether at 0° C. to room temperature, preferably at room temperature.

Hydroxy group of a compound represented by formula (XV) is converted into a diarylhalogenomethane compound using halogenating reagent, described in <Process 1>1), preferably thionyl chloride, at an ice-cool temperature to a temperature for the reflux of the reaction mixture under heating, preferably at a temperature under ice-cool condition, for a time period enough for the reaction, specifically for 5 minutes to 2 hours.

2) Process of producing diarylmethane compounds, represented by formula (IX).

Halogen atom of benzyl position of diaryl halomethane compound by the formula (XII) is removed by the reduction using hydrogenation with Pd-C, metal hydride complex such as sodium borohydride, lithium aluminium hydride, preferably sodium borohydride in DMSO. A protecting group of a compound by a formula (IX) can be deprotected using described above-mentioned "Protective groups in organic synthesis".

In the case of silyl group, it is removed with flouride compounds such as tetrabutylammonium fluoride, cesium fluoride, potassium flouride, HF, preferably tetrabutylammonium fluoride, and converted to deprotected diarylmethane compound by a formula (IX). Then, a compound of the formula (IX) reacts with an azole compound of the formula (X) following the process described in Process 1-1) to synthesize a compound of the formula (I). Herein, the reaction conditions are the same as described in Process 1-1).

According to the process described in Process 1-1), the compound represented by the formula (IX) reacts with an azole compound represented by the formula (X)(wherein when A represents methylene group), for the synthesis of a compound of the formula (I). Herein, the reaction conditions are the same as described in Process 1-1).

Process 5

The compound represented by the formula (I), which is synthesized by any one of Process 1 to Process 4, is further modified of $R^1$, namely the substituent on the benzene ring, in various fashions. Also, an additional substituent can be introduced onto the benzene ring.

Provided that $R^1$ is hydrogen atom, halogen atom, an alkyl group which may be substituted with fluorine atom or an alkoxy group which may be substituted with fluorine atom in the compound of the formula (I), the compound of the formula (I) can be synthesized by any one of Process 1 to Process 4 with higher efficiency.

Alternatively, if $R^1$ in such compound is cyano group, nitro group, alkoxycarbonyl group, carboxyl group, acetyl group, formyl group, alkenyl group or alkynyl group, the compound may preferably be modified, from a compound of the formula (I) with $R^1$ being halogen or hydrogen. Specific examples will be described below.

1) Conversion into cyano group

The compound of the formula (I), having halogen atom as $R^1$, is converted to cyano group by method comprising heating the compound around 250° C. using copper(I) cyanide in the absence of any solvent, or by a method comprising reacting sodium cyanide or potassium cyanide with the compound using as the catalyst a transition metal complex such as palladium complex represent by palladium acetate or nickel complex as tetrakis(triphenylphosphine)nickel.

In using palladium complex, the solvent is used an ether solvent such as ether, THF, dioxane or DME, or a polar solvent such as DMSO or DMF preferably DMF. In using nickel complex, the solvent is used an ether solvent such as ether, THF, dioxane or DME, or a polar solvent such as DMSO or DMF, or an alcohol solvent such as methanol or ethanol, preferably ethanol. The reaction is carried out at room temperature to 200° C., preferably at 70°–120° C.

In the bromine atom as $R^1$, the reaction is carried out preferably with potassium cyanide using palladium acetate as transition metal complex in DMF at 70°–120° C. And in the chlorine atom as $R^1$, the reaction is carried out preferably with potassium cyanide using tetrakis(triphenylphosphine)nickel as transition metal complex in ethanol at 70°–120° C.

The halogen atom as $R^1$ can be converted to cyano group, namely benzonitrile derivative.

2) Conversion into formyl group

Using a suitable metal hydrogen complex such as LiAlH$_4$, DIBAL-H or Red-Al™, preferably using DIBAL-H and using as the solvent an ether solvent such as ether, THF, dioxane or DME or an aromatic hydrocarbon solvent such as benzene, toluene, etc., preferably using as the solvent THF, a benzonitrile derivative produced in 1) is reduced at −78° C. (under cooling with dry ice—acetone) to 100° C., preferably at −78° to 0° C., to convert the $R^1$ into formyl group.

3) Conversion into carboxyl group or alkoxycarbonyl group

The $R^1$ of the benzonitrile derivative produced in 1) is readily converted into carboxyl group, by the hydrolysis thereof under appropriate alkaline conditions with sodium hydroxide or potassium hydroxide for example. Furthermore, through esterification involving dehydration using alcohol in the presence of a mineral acid such as sulfuric acid, hydrochloric acid, etc., an organic acid such as an aromatic sulfonate, or a Lewis acid such as boron fluoride etherate, or via O-alkylation using diazomethane, dialkyl sulfate, alkyl halide, orthoformate, preferably via the use of dialkyl sulfate in the presence of potassium carbonate in acetone, the carboxyl group as $R^1$ is readily modified into alkoxycarbonyl group.

4) Conversion into alkenyl group

Via cross coupling with an organometallic reagent such as a alkenyl magnesium halide, an alkenyl boron compound, an alkenyl tin compound, etc., using a nickel catalyst such as bis(triphenylphosphine)nickel(II) chloride, or palladium catalyst such as tetrakis(triphenylphosphine)palladium [Pd(PPh$_3$)$_4$], bis(triphenylphosphine)palladium(II) chloride [PdCl$_2$(PPh$_3$)$_2$], the compound of the formula (I) with $R^1$ being halogen atom is converted into a derivative with $R^1$ being alkenyl group. Also, the compound of the formula (I) with $R^1$ being halogen atom may be converted into a derivative with $R^1$ being alkenyl group, via Heck reaction using as the catalyst a palladium compound such as Pd(PPh$_3$)$_4$, PdCl$_2$(PPh$_3$)$_2$, palladium acetate, etc., in the presence of an inorganic base such as sodium carbonate or an organic base such as triethylamine.

Via Wittig reaction or via Wittig-Horner-Emmons reaction, the alkenyl derivative can be synthesized from a benzaldehyde compound of the formula (I) with $R^1$ being formyl group, produced in 2). More specifically, using as a base, an inorganic base such as sodium hydroxide, sodium carbonate, etc., an organic base such as $Et_3N$, etc., an alkali metal reagent such as n-BuLi, potassium tert-butoxide (t-BuOK), sodium hydride, etc., preferably using as a base t-BuOK, and also using as a solvent an inactive ether solvent such as ether, THF, dioxane, DME, or a polar solvent such as DMSO, DMF, DMI, preferably using THF, the phosphonium salt or alkyl phosphonate, preferably a alkyl triphenyl phosphonium halide, particularly methyl triphenylphosphonium bromide, is converted into a phosphorous ylide at −78° to 100° C., preferably at room temperature. Subsequently, the ylide compound reacts with a benzaldehyde compound at −78° to 100° C., preferably at room temperature, to convert the compound into a derivative with $R^1$ being alkenyl group.

5) Conversion into alkynyl group

Using pyridine or DMF as the solvent, the reaction of the compound represented by the formula (I) containing halogen atom as $R^1$ with copper acetylide at 80° to 200° C. converts the compound into a derivative with $R^1$ being alkynyl group. Also, the compound represented by the formula (I) with $R^1$ being halogen atom may be converted into a derivative with $R^1$ being alkynyl group, via the reaction with an acetylene compound or a trialkylsilyl derivative thereof or trialkyltin, alkylboron substituted compound, preferably a trialkylsilyl derivative of an acetylene compound, in particular (trimethylsilyl)acetylene, in a solvent including aromatic hydrocarbon solvents such as benzene and toluene, inactive ether solvents such as ether, THF, dioxane and DME, and polar solvent such as DMSO, DMF, and DMI, preferably in DMF as the solvent, using as a base inorganic bases such as sodium hydroxide and sodium carbonate, organic bases such as $Et_3N$ or alkalimetal reagents as a n-BuLi, sodium alkoxide, sodium hydlide, preferably using $Et_3N$ as a base, in the presence of palladium catalysts such as $Pd(PPh_3)_4$, $PdCl_2(PPh_3)_2$, palladium acetate, preferably palladium acetate, at room temperature to 200° C., preferably 100° C. to 200° C. Furthermore, through the action of potassium carbonate, the trialkylsilyl group as $R^1$ can be eliminated from the derivative.

6) Introduction of acetyl group

Still furthermore, the compound of the formula (I) with $R^1$ being hydrogen atom is modified to introduce acetyl group into $R^1$, via Friedel-Craft reaction; in other words, an acetyl group is introduced into $R^1$ by means of a acetyl halide such as acetyl chloride, using as a solvent carbon disulfide, nitrobenzene, tetrachloroethane or in the absence of solvent, preferably using carbon disulfide as a solvent, in the presence of aluminium chloride.

7) Introduction of nitro group

Using a suitable nitration agent such as concentrated nitric acid, fuming nitric acid, alkyl nitrate, salts of nitric acid or nitronium tetrafluoroborate, preferably using sodium nitrate in trifluoroacetic acid, the compound of the formula (I) with $R^1$ being hydrogen atom may be modified into a compound of the formula (I) with $R^1$ being nitro group.

For the use of the compounds of the present invention in pharmaceutical agents, the compounds are formulated into appropriate pharmaceutical preparations by means of an appropriate combination thereof with pharmaceutically acceptable excipients, binders, lubricants, coloring agents, flavoring agents, disintegrators, antiseptic agents, isotonization agents, stabilizing agents, dispersing agents, antioxidants, buffering agents, preservatives, aromatic agents, suspending or emulsifying agents, appropriate carriers or solvents for routine use, sterile water or vegetable oil, for example, if necessary, physiologically acceptable solvents and solubilizers.

Such pharmaceutical preparations includes tablets, capsules, granules, powders, suppositories, vaginal suppositories, syrups, inhalants, external agents, injections and the like, which are administered to patients, orally or parenterally (for example, intravenous injection, intraarterial injection, subcutaneous administration, intramuscular injection, intra-rectal administration, intra-vaginal administration, transdermal absorption or transmucosal absorption and the like).

The dose of the compounds in accordance with the present invention varies depending on the symptom, but the dose for an adult patient is generally within a range of 0.0001 to 10 mg/kg/day, preferably 0.001 to 1 mg/kg/day. The dose may be adjusted appropriately, depending on the conditions of an individual patient.

The entire dose may be administered at a single dose or may be divided into two to six doses for oral or parenteral daily administration or for continuous dosing such as intravenous infusion.

TEST EXAMPLES

Description will follow about the pharmacological actions of representative examples of the compounds in accordance with the present invention.

Experimental Example 1

Inhibitory activity on aromatase from rat ovary.

Using as an enzyme sample the ovarian microsome fraction from a female rat, prepared according to the method described by Brodie et. al, Journal of Steroid Biochemistry, 7, 783, 1976, aromatase inhibitory activity was assayed according to the method by Thompson, et.al, Journal of the Biological Chemistry, 249, 5364, 1974, as follows. To initiate the reaction, NADPH at a final concentration of 0.2 mM was added to a 50 mM potassium phosphate buffer solution (pH 7.4), containing 0.1 mg/ml microsomal preteins, 30 nM [1β-$^3$H] androstenedione and a subject compound of 0.1 nM to 10 nM and the reaction mixture was incubated at 37° C. for 15 minutes, and the reaction was terminated by ice cooling. The suspension of 5% activated charcoal and 0.5% dextran T-70 was added to absorb unreactive substrate, and then the mixture was centrifuged for precipitation, and the radioactivity of [$^3$H]H$_2$O released in the supernatant was counted with a liquid scintillation counter. 6-[(4-chlorophenyl)-(1H-1,2,4-triazol-1-yl)methyl]-1-methyl-1H-benzotriazole (R 76713) as the compound of Example 20 of Japanese Patent Laid-open No. Sho 63-316775 and 5-(p-cyanophenyl)-5,6,7,8-tetrahydroimidazo[1,5-a]pyridine (CGS 16949A) as the compound of Example 1 of Japanese Patent Laid-open No. Sho 61-12688, both of which were developed with attention focused on their higher specificity of aromatase inhibitory action were examined as reference compounds.

In Table 1, the numerical figure shown as IC$_{50}$ is the concentration of a subject compound, for 50% inhibition of aromatase activity.

TABLE 1

| Inhibitory activity on aromatase from rat ovary | |
|---|---|
| Example compound | IC$_{50}$ value (nM) |
| 5 | 6.0 |
| 6 | 9.9 |
| 38 | 0.4 |
| 40 | 0.6 |
| 41 | 0.5 |
| 43 | 0.3 |
| 44 | 7.8 |
| 45 | 3.3 |
| 46 | 0.4 |
| 47 | 1.6 |
| 48 | 0.9 |
| 49 | 1.5 |
| 50 | 0.5 |
| 51 | 1.2 |
| 52 | 0.4 |
| 53 | 0.8 |
| 55 | 1.4 |
| 56 | 0.3 |
| 58 | 0.3 |
| 64 | 0.6 |
| 67 | 0.6 |
| 68 | 2.6 |
| 71 | 1.2 |
| 79 | 0.7 |
| 80 | 1.9 |
| CGS16949A | 1.0 |
| R76713 | 1.4 |

Distinctive aromatase inhibitory activity was observed in all of the compounds of the present invention.

Experimental Example 2

Decreasing activity on blood estrogen

Decreasing activity on blood estrogen was assayed by a modification of the method by Waters, et. al, Journal of Steroid Biochemistry, 32, 781, 1989. More specifically, pregnant mare serum gonadotropin (PMSG) was subcutaneously administered to female SD rats aged 3 weeks, at a dose of 200 IU/rat. After 72 hours, a test compound dissolved in an aqueous 20% propylene glycol solution was orally given at a dose of 0.001 to 0.1 mg/kg. Four hours after the dosing of the test compound, blood was sampled, and plasma estradiol was messuered by radioimmunoassay(RIA). The decreasing ratio (%) in plasma estradiol levels was calculated by comparing with control groups. As reference compounds, R 76713 and CGS 16949A were tested. The results are shown in Table 2.

TABLE 2

| | Decreasing activity on blood estrogen | | |
|---|---|---|---|
| | Ratio in plasma estradiol decrease (%) Doses (mg/kg) | | |
| Examples | 0.001 | 0.01 | 0.1 |
| 38 | — | — | 44 |
| 41 | — | 46 | 70 |
| 43 | — | 41 | 69 |
| 44 | — | — | 23 |
| 46 | — | 36 | — |
| 48 | — | 30 | — |
| 50 | — | 59 | — |
| 52 | 22 | 77 | 91 |
| 80 | — | — | 49 |

TABLE 2-continued

| | Decreasing activity on blood estrogen | | |
|---|---|---|---|
| | Ratio in plasma estradiol decrease (%) Doses (mg/kg) | | |
| Examples | 0.001 | 0.01 | 0.1 |
| R76713 | — | 60 | 85 |
| CGS16949A | 44 | 81 | 94 |

—: Not tested

All of the compounds of the present invention exerted highly potent decreasing effect on the blood estrogen levels.

Experimental Example 3

The effects on the synthesis of various steroid hormones

The effects on the synthesis of various steroid hormones were examined according to a modification of the method by Waters, et. al, Journal of Steroid Biochemistry, 32, 781, 1989. For more detailed description, a subject compound dissolved in aqueous 20% propylene glycol was given orally to male SD rats aged 7 weeks at a dose of 0.1 to 10 mg/kg. Three hours later, adrenocortictropic hormone (ACTH) and lutenizing hormone-releasing hormone (LH-RH) were intramuscularly administered to the rats at doses of 25 µg/rat and 40 ng/rat, respectively. One hour later, blood was sampled, and plasma aldosterone, corticosterone, progesterone, 17α-hydroxyprogesterone were messured by RIA. The change ratio in % were calculated by comparing with control group. As reference compounds, R 76713 and CGS 16949A were given at doses of 10 mg/kg and 1 mg/kg, respectively, at maximum.

The hormones to be assayed were the final products or major intermediates of steroid hormone synthetic pathway, as well as principal steroid hormones which are synthesized in adrenal cortex and gonads of males and females. Therefore, it is believed that the levels of these hormones in blood may change if a pharmaceutical agent has effects on some enzyme involved in the steroid hormone synthetic pathway.

Even at the highest doses, neither the compound of Example 41 nor the compound of Example 52 in accordance with the present invention had any effect on plasma levels of corticosterone, progesterone and testosterone, which is also the case with R 76713 and CGS 16949A. On the contrary, the reference compounds did change the plasma levels of aldosterone and 17α-hydroxyprogesterone. The results are shown in Tables 3 and 4.

TABLE 3

| | Lowering effect on plasma aldosterone | | | |
|---|---|---|---|---|
| | Decrease in plasma aldosterone (%) Doses (mg/kg) | | | |
| Example compounds | 0.1 | 1 | 3 | 10 |
| 41 | — | — | NE | NE |
| 52 | — | — | NE | NE |
| R76713 | — | — | NE | 28 |
| CGS16949A | 37 | 55 | — | — |

NE: Not effected
—: Not tested

TABLE 4

| | Elevating effect on plasma 17α-hydroxyprogesterone | | | |
|---|---|---|---|---|
| Example | Elevation in plasma 17α-hydroxyprogesterone (%) Doses (mg/kg) | | | |
| compounds | 0.1 | 1 | 3 | 10 |
| 41 | — | — | NE | NE |
| 52 | — | — | NE | NE |
| R76713 | — | — | 276 | 460 |
| CGS16949A | 169 | 313 | — | — |

NE: Not effected
—: Not tested

Neither the compound of Example 41 nor the compound of Example 52 in accordance with the present invention had any effect on any steroid hormone level in blood at a dose of 10 mg/kg corresponding to 1,000 fold to 10,000 fold of the dose at which blood estrogen is lowered. On the contrary, one control compound, R 76713, elevated plasma 17α-hydroxyprogesterone level at a dose of 3 mg/kg or more, while at a dose of 10 mg/kg or more, the compound decreased plasma aldosterone level. At a dose of 0.1 mg/kg or more, the other control compound, CGS 16949A, lowered plasma aldosterone level while elevating 17α-hydroxyprogesterone level. Hence, the discrepancy of these reference compounds between the dose for lowering plasma estrogen level and the effective dose on aldosterone and/or 17α-hydroxyprogesterone is 100 fold or less.

Experimental Example 4

Acute toxicity test

Acute toxicity of the present compounds was tested. The compound of Example 52 in accordance with the present invention was given at an oral dose of 10 mg/kg to male Wistar rats aged 9 weeks. After 7-day observation period, no death was observed, without any abnormality in body weight or general behavior.

The results of Experimental Examples 1 and 2 indicate that the compounds of the present invention have remarkable aromatase inhibitory activity in vitro and also decrease blood estrogen level in vivo at a lower dose in a reliable fashion. Thus, it is expected that the compounds of the present invention should be useful as aromatase inhibitory agents.

The results of Experimental Example 3 indicate that the compounds of the present invention have higher selectivity for aromatase as the target enzyme, and therefore, the compounds lower estrogen in vivo at higher specificity. For the application of pharmaceutical preparations to patients with estrogen-dependent diseases including breast cancer requiring long-term dosing, any effect on blood levels of a variety of steroid hormones which is necessary to homeostasis may involve a risk of the occurrence of severe side effects. Therefore, it is needless to say that a pharmaceutical agent with higher specificity to aromatase is desired. From such respect, the substances of the present invention will be highly safe agents for clinical use with less side effects, compared with other compounds under development.

The results of Experimental Example 4 demonstrate that the compounds of the present invention did not induce any abnormality in experimental animals. The compounds may have high safety.

Thus, it is shown that the azolyl methyl phenyl derivatives in accordance with the present invention exert superior aromatase inhibitory activity in vitro and that the derivatives significantly lower blood estrogen level and have higher specificity for aromatase inhibition in vivo in animal experiments using an experimental rat model, in addition to the finding that the derivatives are highly safe. It was demonstrated that the azolyl methyl phenyl derivatives in accordance with the present invention are superior in at least any one of the characteristic properties.

The azolyl methyl phenyl derivatives in accordance with the present invention are extremely useful as the prophylactic agents and/or therapeutical agents for estrogen-dependent diseases include estrogen dependent-cancers (ex. breast cancer, ovarian cancer, endometrium cancer. etc.), endometriosis, uterine leiomyoma, benign breast diseases, mastopathy, premature labor, benign prostatic hyperplasia, prostate cancer, precocious puberty, gynecomastia, male infertility relating to oligospermia and cholelithiasis. Also, the derivatives are useful as contraceptive agents for females.

The results of Experimental Examples 1 to 3 indicate that the compounds of the present invention are useful as aromatase inhibitory agents for use in the form of reagents and in animals.

The present invention will now be explained in details in examples, but the invention is not limited to these examples.

NMR analysis was carried out by JEOL FX90A FT-NMR (manufactured by Nippon Densi, Co. Ltd.; symbol "*" was marked with the data;) or by JEOL JNM-EX270 FT-NMR (manufactured by Nippon Densi, Co. Ltd.); IR was analyzed by HORIBA FT-200 (manufactured by Horiba, Co. Ltd.); melting point was measured by Mettler FP80 or FP90 (both were manufactured by Mettler, Co. Ltd.); HPLC was performed by TOSOH CCPD (manufactured by TOSOH, Co. Ltd.) or by SHIMADZU LC-10A (manufactured by SHIMADZU, Co. Ltd.).

Example 1

Synthesis of 1-(4-chloro-2-methylphenoxy)naphthalene

4-Chloro-2-methylphenol (10 g) and powdery KOH (4.6 g) were mixed together and then heated at 150° C. for 1 hour. After cooling down to 100° C., DMI (50 ml) was added to the resulting mixture for dissolving the mixture. Subsequently, 1-bromonaphthalene (14.5 g) and copper powder (350 mg) were added to the resulting solution, which was then heated under stirring at 130° C. for 3 hours. After leaving the solution to stand at room temperature, 1N NaOH was added to the solution, and then, the product was extracted with ether. The ether layer was washed with 1N NaOH, washed twice with water, and washed once in saturated sodium chloride solution. After drying over anhydrous sodium sulfate, the solvent was removed under reduced pressure. The residue was purified by chromatography on a silica gel column (hexane:ether=99:1) to give the title compound (2 g; 11%).

Example 2

Synthesis of 2-(4-chloro-2-methylphenoxy)naphthalene

Following Example 1, the title compound was synthesized (yield; 9%) from 4-chloro-2-methylphenol and 2-bromonaphthalene.

Example 3

Synthesis of 1-(2-bromomethyl-4-chlorophenoxy)naphthalene 1-(4-Chloro-2-methylphenoxy)naphthalene (1.8 g) from Example 1 was dissolved in carbon tetrachloride (10 ml), followed by addition of NBS (1.2 g) and a catalytic amount of benzoyl peroxide under reflux for 2 hours. After leaving the solution to stand at room temperature, insoluble materials were filtered off, and the filtrate was concentrated under reduced pressure. The residue was purified by chromatography on a silica gel column (hexane:ether=99:1) to give the title compound (900 mg; 39%).

Example 4

Synthesis of 2-(2-bromomethyl-4-chlorophenoxy)naphthalene

Following Example 3, the title compound was synthesized from 2-(4-chloro-2-methylphenoxy)naphthalene is obtained in Example 2.

Example 5

Synthesis of 1-[5-chloro-2-(1-naphthyloxy)benzyl]-1H-imidazole 1-(2-Bromomethyl-4-chlorophenoxy)naphthalene (400 mg) from Example 3 was dissolved in acetonitrile (20 ml), followed by addition of imidazole (235 mg) and cesium carbonate (1.1 g) under reflux for 10 minutes. After leaving the solution to stand at room temperature, the solvent was removed under reduced pressure. The residue was purified by chromatography on a silica gel column (methylene chloride:methanol=99:1) to give the title compound (270 mg; 70%). The purity of the compound was determined by HPLC, which was of 99.9%.

Examples 6 and 7

Following Example 5, compounds shown in Table 5 were synthesized.

TABLE 5

| Examples | Name of compound | Yield (%) | Purity (%) |
|---|---|---|---|
| 6 | 1-[5-Chloro-2-(2-naphthyloxy)benzyl]-1H-imidazole | 62 | 98.2 |
| 7 | 1-[5-Chloro-2-(1-naphthyloxy)benzyl]-1H-1,2,4-triazole | 66 | 97.7 |

Example 8

Synthesis of 5-chloro-2-nitro-N-trifluoroacetylaniline

5-Chloro-2-nitroaniline (25 g) was dissolved in methylene chloride (250 ml), followed by addition of pyridine (11.7 g). A solution of trifluoroacetic anhydride (20 ml) in methylene chloride (50 ml) was added dropwise to the resulting mixture under ice cooling under stirring for 2 hours. Subsequently, water was added to the reaction mixture solution to separate the methylene chloride layer, which was then dried over anhydrous sodium sulfate. By removal of the solvent under reduced pressure, the title compound was given (38 g; 98%).

Example 9

Synthesis of 5-chloro-N-methyl-2-nitro-N-trifluoroacetylaniline

5-Chloro-2-nitro-N-trifluoroacetylaniline (38 g) from Example 8 was dissolved in acetone (300 ml), followed by addition of potassium carbonate (19.5 g). To the mixture was added dropwise dimethyl sulfate (13.4 ml) for subsequent stirring for 1.5 hours. After filtering off insoluble inorganic materials, the resulting material was washed with ethyl acetate. Removal of the solvent under reduced pressure, hexane was added to the residue under stirring, to separate the crystal by filtration. By washing the crystal further with ether-hexane mixture solution, the title compound was given (33 g; 83.5%).

Example 10

Synthesis of 5-chloro-N-methyl-2-nitroaniline

5-Chloro-N-methyl-2-nitro-N-trifluoroacetylaniline (30 g) from Example 9 was dissolved in methanol (300 ml), followed by addition of an aqueous 15% NaOH solution and subsequent addition of methanol (50 ml) under stirring for 3 hours. The reaction mixture solution was poured into water (400 ml), and the precipitate was given by filtration, which was then washed with water. The precipitate was dissolved in methylene chloride (300 ml), and then the methylene chloride layer was washed with water and saturated sodium chloride solution to dry the product over anhydrous sodium sulfate. After removal of the solvent under reduced pressure, the title compound was given (19 g; 96%).

Example 11

Synthesis of 4-bromo-2-hydroxymethylphenol

Under ice cooling, the solution of 5-bromosalicylic acid (21.7 g) in ether (200 ml) was slowly added dropwise to the suspension of $LiAlH_4$ (5.7 g) in ether (200 ml). After stirring at room temperature for 30 minutes, the reaction solution was slowly poured into 3N HCl with floating ice for extraction with ethyl acetate. The organic phase was washed with saturated sodium chloride solution, and dried over anhydrous sodium sulfate. The oily residue generated after the evaporation of the solvent under reduced pressure was crystallized from ether-hexane, and the crystal was filtered, to give the title compound (15.5 g; 76.5%).

Examples 12 to 16

Following Example 11, the synthesis of the compounds shown in Table 6 was carried out.

TABLE 6

| Examples | Name of compound | Yield (%) |
|---|---|---|
| 12 | 4-Chloro-2-hydroxymethylphenol | 70 |
| 13 | 2-Hydroxymethyl-4-iodophenol | 75 |
| 14 | 4-Fluoro-2-hydroxymethylphenol | 71 |
| 15 | 5-Chloro-2-hydroxymethylphenol | 78 |
| 16 | 4-Chloro-2-(hydroxymethyl)thiophenol | 69 |

Example 17

Synthesis of 2-hydroxymethyl-4-methoxyphenol

Under ice cooling, the solution of 5-methoxysalicylaldehyde (5 g) in ether (20 ml) was slowly added dropwise to the suspension of $LiAlH_4$ (0.75 g) in ether (50 ml). After stirring at room temperature for 2 hours, another addition of $LiAlH_4$ (0.5 g) was carried out under ice cooling, with subsequent stirring at room temperature for 30 minutes. To the reaction solution was added ice carefully, followed by sequential addition of 1N HCl and ether. After filtering off insoluble materials using Celite™, the ether layer was separated from the filtrate, and then, the aqueous phase was further extracted with ether. The combined ether layers were washed with saturated sodium chloride solution, and dried over anhydrous sodium sulfate. The solvent was removed under reduced pressure, and the residue was washed with ether-hexane and filtered to give the title compound (3.9 g; 77%).

Example 18

Synthesis of 2-hydroxymethyl-4-(trifluoromethoxy)phenol

Following Example 17, the title compound was given (2.04 g; 100%) from 5-(trifluoromethoxy)salicylaldehyde (2 g).

Example 19

Synthesis of 4-chloro-2-(1H-imidazol-1-ylmethyl)phenol

4-Chloro-2-methylphenol (9 g) was dissolved with pyridine (30 ml), followed by addition of acetic anhydride (7.2 ml) under ice cooling for 2 hours stirring at room temperature. Then, ether was added to the reaction solution, and washed with water (×3), and 1N HCl (×1), and dried over anhydrous sodium sulfate. By removal of the solvent under reduced pressure, 2-acetoxy-5-chlorotoluene (11 g; 95%) was given.

The acetoxy derivative (8.75 g) was dissolved in carbon tetrachloride (100 ml), followed by addition of NBS (9 g) and benzoyl peroxide (30 mg) ueder reflux for 2 hours. After leaving the mixture to stand at room temperature, insoluble materials were filtered off, and the filtrate was washed with saturated sodium hydrogen carbonate solution and dried over anhydrous sodium sulfate. By removal the solvent under reduced pressure, 2-acetoxy-5-chlorobenzyl bromide was given. 6 g of the 2-acetoxy-5-chlorobenzyl bromide was dissolved in acetonitrile (100 ml), followed by addition of imidazole (1.5 g) and cesium carbonate (7.2 g) for stirring at room temperature for 1 hour. Further addition of imidazole (1.5 g) was carried out for subsequent reflux for 30 minutes.

After the reaction solution was left to stand at room temperature, the solution was poured into water and extracted twice with ethyl acetate. The organic layers were combined together, which was then washed with saturated sodium chloride solution and dried over anhydrous sodium sulfate. After removal of the solvent under reduced pressure, the residue was dissolved in methanol followed by addition of 1N NaOH under stirring at room temperature for 1 hour, and then methanol was removed. After addition of water to the residue, the aqueous layer was extracted three times with ethyl acetate. The organic layers were combined together, which was then washed with saturated sodium chloride solution and dried over anhydrous sodium sulfate. Under reduced pressure, the solvent was removed, and the resulting residue was purified by chromatography on a silica gel column (methylene chloride:methanol=49:1) to give the crystal. The crystal was washed with ether to yield the title compound (1.45 g; 31.5%).

Example 20

Synthesis of 4-chloro-2-(1H-1,2,4-triazol-1-ylmethyl)phenol
Process A:

The intermediate 1-acetoxy-5-chlorobenzylbromide (6 g) produced in Example 19 was dissolved in acetonitrile (60 ml), followed by addition of 1H-1,2,4-triazole (1.15 g) and cesium carbonate (7.5 g) for reflux for 1 hour. After leaving the solution to stand at room temperature, insoluble materials were filtered off and then washed with ethyl acetate. The filtrate and the washing solution were combined together, to remove the solvent under reduced pressure. To the residue was added 1N HCl for neutralization and subsequent extraction with methylene chloride. The organic layer was washed with saturated sodium chloride solution, and dried over anhydrous sodium sulfate. After removal of the solvent under reduced pressure, the residue was purified by chromatography on a silica gel column (methylene chloride:methanol=49:1) to give the title compound (1.5 g; 31.5%).

Process B:

The mixture of 4-chloro-2-hydroxymethylphenol (25.3 g) from Example 12 and 1H-1,2,4-triazole (32.7 g) was stirred at about 160° C. for 1 hour. After left to stand for cooling, the mixture was solidified into crystal, which was then recrystallized from ethanol and collected to give the title compound (31.7 g; 73%).

Example 21

Synthesis of 2-(1H-1,2,4-triazol-1-ylmethyl)phenol

The mixture of 2-hydroxymethylphenol (25.3 g) and 1H-1,2,4-triazole (15.5 g) was agitated at about 160° C. for 1 hour. After left to stand for cooling, the mixture was solidified into crystal, which was then recrystallized from ethanol and collected to give the title compound (27 g; 76 %).

Examples 22 to 27

Following Example 21, the synthesis of the compounds shown in Table 7 were performed.

TABLE 7

| Examples | Name of compound | Yield (%) |
|---|---|---|
| 22 | 4-Bromo-2-(1H-1,2,4-triazol-1-ylmethyl)phenol | 71 |
| 23 | 4-Fluoro-2-(1H-1,2,4-triazol-1-ylmethyl)phenol | 65 |
| 24 | 4-Iodo-2-(1H-1,2,4-triazol-1-ylmethyl)phenol | 22 |
| 25 | 4-Methoxy-2-(1H-1,2,4-triazol-1-ylmethyl)phenol | 66 |
| 26 | 2-(1H-1,2,4-triazol-1-ylmethyl)-4-(trifluoromethoxy)phenol | 64 |
| 27 | 5-Chloro-2-(1H-1,2,4-triazol-1-ylmethyl)phenol | 78 |

Example 28

Synthesis of 5-[4-chloro-2-(1H-imidazol-1-ylmethyl)phenoxy]-N-methyl-2-nitroaniline 4-Chloro-2-(1H-imidazol-1-ylmethyl)phenol (210 mg) from Example 19 and powdered KOH (66 mg) were mixed together, and melting at 130° C. under heating. The reaction mixture was dried under reduced pressure, followed by addition of DMI (1 ml), 5-chloro-N-methyl-2-nitroaniline (190 mg) from Example 10 and a smaller amount of copper powder for heating at 130° C. for 3 hours. After the mixture was left to stand at room temperature, water and ethyl acetate was added to the resulting mixture, and then the copper powder was filtered off for extraction in ethyl acetate. The organic layer was washed with saturated sodium chloride solution, and dried over anhydrous sodium sulfate. After removal of the solvent under reduced pressure, the residue was purified by chromatography on a silica gel column (methylene chloride:methanol=99:1) to give the title compound (250 mg; 69.5%).

Example 29

Synthesis of 5-[4-chloro-2-(1H-1,2,4-triazol-1-ylmethyl)phenoxy]-N-methyl-2-nitroaniline 4-Chloro-2-(1H-1,2,4-triazol-1-ylmethyl)phenol (840 mg) from example 20 and powdery KOH (260 mg) were mixed together, for heating and melting at 150° C. The reaction mixture was dried under reduced pressure, followed by addition of DMI (4 ml), 5-chloro-N-methyl-2-nitroaniline (750 mg) from Example 10 and a smaller amount of copper powder for heating at 130° C. for 3 hours. After the mixture was left to stand at room temperature, water and ethyl acetate was added to the resulting mixture, and then the copper powder was filtered off for extraction with ethyl acetate. The organic layer was washed with saturated sodium chloride solution, and dried over anhydrous sodium sulfate. After removal of the solvent under reduced pressure, the residue was purified by chromatography on a silica gel column (methylene chloride:methanol=99:1) to give the title compound (750 mg; 52%).

Example 30

Synthesis of 5-[4-bromo-2-(1H-1,2,4-triazol-1-ylmethyl)phenoxy]-N-methyl-2-nitroaniline At room temperature, NaOMe (2.6 g) was gradually added to a solution of 4-bromo-2-(1H-1,2,4-triazol-1-ylmethyl)phenol (11.4 g) from Example 22 in methanol (200 ml). After stirring at room temperature for 15 minutes, concentration under reduced pressure was carried out prior to drying. To the resulting product were added DMI (150 ml), 5-chloro-N-methyl-2-nitroaniline (8.4 g) from Example 10 and copper powder (0.3 g), for heating at 130° C. for 3 hours. After the mixture was left to stand at room temperature, water and ethyl acetate was added to the resulting mixture, the copper powder was filtered off. The organic layer was washed with saturated sodium chloride solution, and dried over anhydrous sodium sulfate. After removal of the solvent under reduced pressure, the residue was purified by chromatography on a silica gel column (methylene chloride:methanol=39:1) to recover the title compound (11.4 g; 62.5%).

Examples 31 to 36

Following Example 30, synthesis of the compounds shown in Table 8 was carried out.

TABLE 8

| Examples | Name of compound | Yield (%) |
|---|---|---|
| 31 | N-Methyl-2-nitro-5-[2-(1H-1,2,4-triazol-1-ylmethyl)phenoxy]aniline | 61 |
| 32 | 5-[4-Fluoro-2-(1H-1,2,4-triazol-1-ylmethyl)phenoxy]-N-methyl-2-nitroaniline | 72 |
| 33 | 5-[4-Iodo-2-(1H-1,2,4-triazol-1-ylmethyl)phenoxy]-N-methyl-2-nitroaniline | 33 |
| 34 | 5-[4-Methoxy-2-(1H-1,2,4-triazol-1-ylmethyl)phenoxy]-N-methyl-2-nitroaniline | 77 |
| 35 | N-Methyl-5-[2-(1H-1,2,4-triazol-1-ylmethyl)-4-(trifluoromethoxy)phenoxy]-2-nitroaniline | 64 |
| 36 | 5-[5-Chloro-2-(1H-1,2,4-triazol-1-ylmethyl)phenoxy]-N-methyl-2-nitroaniline | 39 |

Example 37

Synthesis of 5-[4-chloro-2-(1H-1,2,4-triazol-1-ylmethyl)phenoxy]-2-nitroaniline

At room temperature, NaOMe (7.1 g) was gradually added to a solution of 4-chloro-2-(1H-1,2,4-triazol-1-ylmethyl)phenol (25 g) from Example 20 in methanol (500 ml). After stirring at room temperature for 1 hour, the mixture was evaporated under reduced pressure for drying. To the resulting product were added DMI (500 ml), 5-chloro-2-nitroaniline (20.6 g) and copper powder (0.76 g) for heating at 130° C. for 2.5 hours. After the mixture was left to stand at room temperature, water and ethyl acetate was added to the resulting mixture, the copper powder was filtered off. The organic layer was washed with saturated sodium chloride solution, and dried over anhydrous sodium sulfate. After removal of the solvent under reduced pressure, the residue was washed with methylene chloride to give the title compound (11 g; 27%).

Example 38

Synthesis of 6-[4-chloro-2-(1H-imidazol-1-ylmethyl)phenoxy]-1-methyl-1H-benzotriazole 5-[4-Chloro-2-(1H-imidazol-1-ylmethyl)phenoxy]-N-methyl-2-nitroaniline (250 mg) from Example 28 was dissolved in acetic acid (3 ml), followed by gradual addition of zinc powder (250 mg) at room temperature. After the addition, ethyl acetate was added to filter off insoluble materials. To the filtrate was added saturated sodium hydrogencarbonate solution carefully for separation. The organic layer was washed with saturated sodium chloride solution, and dried over anhydrous sodium sulfate. After removal of the solvent under reduced pressure, the residue was purified by chromatography on a silica gel column (methylene chloride:methanol=97:3) to give 4-[4-chloro-2-(1H-imidazol-1-ylmethyl)phenoxy]-2-methylaminoaniline (160 mg; 70%).

The amino compound (140 mg) was dissolved in 6N-HCl (1.5 ml), to which was then added an aqueous solution (0.1 ml) of sodium nitrite (60 mg) under ice cooling, the reaction temperature was elevated to room temperature, which was then stirred as it was for 20 minutes. Under ice cooling, subsequently, the mixture was neutralized with an s aqueous sodium hydrogen carbonate solution, and the mixture was extracted with methylene chloride. The organic layer was dried over anhydrous sodium sulfate, while the solvent was distilled off under reduced pressure. The resulting residue was purified by chromatography on a silica gel column (methylene chloride:methanol=49:1) to give the title compound (76 mg; 52%). The purity of the compound was 94.7% by HPLC.

Example 39

Synthesis of 4-[4-chloro-2-(1H-1,2,4-triazol-1-ylmethyl)phenoxy]-1,2-phenylenediamine 5-[4-Chloro-2-(1H-1,2,4-triazol-1-ylmethyl)phenoxy]-2-nitroaniline (11 g) from Example 37 was dissolved in acetic acid (100 ml), followed by gradual addition of zinc powder (12.5 g) under water cooling. After the addition, insoluble materials were filtered off, and the filtrate was concentrated under reduced pressure. To the residue was added ethyl acetate, and to the resulting solution was added carefully saturated sodium hydrogen carbonate solution to make the solution alkaline. The organic phase was washed with saturated sodium chloride solution, and dried over anhydrous sodium sulfate. After removal of the solvent under reduced pressure, the residue was crystallized from chloroform (100 ml) and ethanol (10 ml), and the deposited crystal was filtered to give the title compound (4.98 g; 50%).

Example 40

Synthesis of 5-[4-chloro-2-(1H-1,2,4-triazol-1-ylmethyl)phenoxy]-1H-benzotriazole 4-[4-Chloro-2-(1H-1,2,4-triazol-1-ylmethyl)phenoxy]-1,2-phenylenediamine (3.2 g) from Example 39 was dissolved with 10% $H_2SO_4$ (30 ml) under ice cooling, followed by addition of an aqueous solution (3 ml) of sodium nitrite (1.4 g), and the temperature of the resulting solution was raised up to room temperature for stirring for 2 hours. The solution was neutralized, with an aqueous sodium hydrogen carbonate, and then extracted twice with methylene chloride. The organic phase was dried over anhydrous sodium sulfate, and the solvent was removed under reduced pressure. The resulting residue was washed with ether, to give the title compound (3 g; 91%). The purity of the compound was 99.1% by HPLC.

Examples 41 and 42

Synthesis of 6-[4-chloro-2-(1H-1,2,4-triazol-1-ylmethyl)phenoxy]-1-methyl-1H-benzotriazole and 5-[4-chloro-2-(1H-1,2,4-triazol-1-ylmethyl)phenoxy]-1-methyl-1H-benzotriazole To the suspension of 5-[4-chloro-2-(1H-1,2,4-triazol-1-ylmethyl)phenoxy]-1H-benzotriazole (3 g) from Example 40 and potassium carbonate (1.27 g) in DMF (15 ml) was added dimethyl sulfate (0.96 ml) for stirring at room temperature for 2 hours. To the reaction solution were added ethyl acetate and water to separate the organic layer, which was then washed with saturated sodium chloride solution and dried over anhydrous sodium sulfate. Under reduced pressure, the solvent was removed of, and the resulting residue was purified by chromatography on a silica gel column. From a fraction eluted with methylene chloride, 5-[4-chloro-2-(1H-1,2,4-triazol-1-ylmethyl)phenoxy]-2-methyl-2H-benzotriazole was given (0.67 g; 21%). From a fraction eluted with methylene chloride:methanol (=99:1 to 49:1), 6-(1-methyl)-1H-benzotriazoyloxy derivative and 5-(1-methyl)-1H-benzotriazoyloxy derivative were given as a mixture. The mixture was purified again by chromatography on a silica gel column. From a fraction eluted with ethyl acetate:hexane (=3:1 to 4:1), 6-[4-chloro-2-(1H-1,2,4-triazol-1-ylmethyl)phenoxy]-1-methyl-1H-benzotriazole (Example 41) was given (0.71 g; 23%). The purity of the product was 94.7% by HPLC. From a fraction eluted with ethyl acetate:hexane (=9:1), 5-[4-chloro-2-(1H-1,2,4-triazol-1-ylmethyl)phenoxy]-1-methyl-1H-benzotriazole (Example 42) was given (0.44 g; 14%). The purity of the product was 99.7% by HPLC.

The compound of Example 41, i.e. 6-[4-chloro-2-(1H-1,2,4-triazol-1-ylmethyl)phenoxy]-1-methyl-1H-benzotriazole may be synthesized by the following another method.

5-[4-Chloro-2-(1H-1,2,4-triazol-1-ylmethyl)phenoxy]-N-methyl-2-nitroaniline (720 mg) from Example 29 was dissolved in acetic acid (5 ml), followed by gradual addition of zinc powder (700 mg) at room temperature. After the addition, ethyl acetate was added to filter off insoluble materials, and saturated sodium hydrogen carbonate solution was added to the filtrate carefully for separation. The organic layer was washed with saturated sodium chloride solution, and dried over anhydrous sodium sulfate. After removal of the solvent under reduced pressure, the residue was purified by chromatography on a silica gel column (ethyl acetate:hexane:methanol=80:20:1), to given 4-[4-chloro-2-(1H-1,2,4-triazol-1-ylmethyl)phenoxy]-2-methylaminoaniline (400 mg; 60.5%).

The amino compound (280 mg) was dissolved in 10% $H_2SO_4$ (5 ml) under ice cooling, followed by addition of an aqueous solution (0.2 ml) of sodium nitrite (120 mg), and the temperature of the resulting solution was raised up to room temperature for stirring for 1 hour. Neutralization with an aqueous sodium hydrogencarbonate solution was carried out, and then the solution was extracted twice with methylene chloride. The organic phase was dried over anhydrous sodium sulfate, and the solvent was removed under reduced pressure. The resulting residue was purified by chromatography on a silica gel column (methylene chloride:methanol= 99:1 to 98:2), to give the title compound (200 mg; 69%).

Example 43

Synthesis of 6-[4-bromo-2-(1H-1,2,4-triazol-1-ylmethyl)phenoxy]-1-methyl-1H-benzotriazole 5-[4-Bromo-2-(1H-1,2,4-triazol-1-ylmethyl)phenoxy]-N-methyl-2-nitroaniline (11 g) from Example 30 was dissolved with acetic acid (120 ml), followed by gradual addition of zinc powder (10.6 g) at room temperature. After the addition, stirring was carried out for 5 minutes. Ethyl acetate was added to filter off insoluble materials, and the filtrate was concentrated under reduced pressure. Saturated sodium hydrogen carbonate solution was added to the residue carefully for alkali adjustment. The organic layer was washed with saturated sodium chloride solution, and dried over anhydrous sodium sulfate. After removal of the solvent under reduced pressure, the crude residue, i.e. 4-[4-bromo-2-(1H-1,2,4-triazol-1-ylmethyl)phenoxy]-2-methylaminoaniline was dissolved in 10% $H_2SO_4$ (120 ml) under ice cooling, followed by addition of an aqueous solution (20 ml) of sodium nitrite (3.75 g), and the temperature of the resulting solution was raised up to room temperature for stirring for 1 hour. Neutralization with an aqueous sodium hydrogencarbonate solution was carried out, and the solution was extracted twice with methylene chloride. The organic phase was dried over anhydrous sodium sulfate, and the solvent was removed under reduced pressure. The resulting residue was purified by chromatography on a silica gel column (methylene chloride:methanol=40:1 to 20:1), to give the title compound (4.55 g; 43%). The purity of the compound was 99.2% by HPLC.

Example 44

Synthesis of 1-methyl-6-[2-(1H-1,2,4-triazol-1-ylmethyl)phenoxy]-1H-benzotriazole
Process A:

Following Example 43, the title compound was synthesized (4.18 g; 81%) from N-methyl-2-nitro-5-[2-(1H-1,2,4-triazol-1-ylmethyl)phenoxy]aniline (5.5 g) from Example 31. The purity of the compound was 99.7% by HPLC.
Process B:

6-[4-Bromo-2-(1H-1,2,4-triazol-1-ylmethyl)phenoxy]-1-methyl-1H-benzotriazole (77 mg) from Example 43 was suspended in DMF(1 ml) —MeOH (1 ml), followed by addition of 10% palladium-carbon (10 mg), and the reaction system was then hydrogen atomosphere, and the mixture was stirred at room temperature for 7 hours. Ethyl acetate was added to filter off the catalyst, and the reaction solution was washed sequentially with sodium hydrogencarbonate solution, water and saturated sodium chloride solution, and dried over anhydrous sodium sulfate. Then, the solvent was removed under reduced pressure. To the residue was added ether for crystallization, to give pale yellow crystal(53 mg; 87%).

Examples 45 to 49

Following Example 43, synthesis of the compounds in Table 9 herein below were undertaken.

TABLE 9

| Examples | Name of compound | Yield (%) | Purity (%) |
|---|---|---|---|
| 45 | 6-[4-Fluoro-2-(1H-1,2,4-triazol-1-ylmethyl)phenoxy]-1-methyl-1H-benzotriazole | 47 | 100 |
| 46 | 6-[4-Iodo-2-(1H-1,2,4-triazol-1-ylmethyl)phenoxy]-1-methyl-1H-benzotriazole | 65 | 98.0 |
| 47 | 6-[4-Methoxy-2-(1H-1,2,4-triazol-1-ylmethyl)phenoxy]-1-methyl-1H-benzotriazole | 80 | 99.4 |
| 48 | 1-Methyl-6-[4-(trifluoromethoxy)-2-(1H-1,2,4-triazol-1-ylmethyl)phenoxy]-1H-benzotriazole | 78 | 100 |
| 49 | 6-[5-Chloro-2-(1H-1,2,4-triazol-1-ylmethyl)phenoxy]-1-methyl-1H-benzotriazole | 73 | 100 |

Example 50

Synthesis of 1-methyl-6-[4-nitro-2-(1H-1,2,4-triazol-1-ylmethyl)phenoxy]-1H-benzotriazole The suspension of 1-methyl-6-[2-(1H-1,2,4-triazol-1-ylmethyl)phenoxy]-1H-benzotriazole (0.5 g) from Example 44, sodium nitrate (0.28 g) and trifluoroacetic acid (5 ml) was stirred at room temperature for 3 days. Stirring was done for another day after further addition of sodium nitrate (0.28 g), and the reaction solution was neutralized with sodium hydrogen carbonate solution, prior to extraction in ethyl acetate. The organic layer was washed with saturated sodium chloride solution, and dried over anhydrous sodium sulfate, prior to removal of the solvent under reduced pressure. The resulting crude crystal in pale yellow was washed with ethyl acetate to give white crystal, which was then recrystallized three times for methanol to give the title compound (0.15 g; 25%). The purity of the compound was 98.8% by HPLC.

Example 51

Synthesis of 4-[6-(1-methyl-1H-benzotriazoyloxy)]-3-(1H-1,2,4-triazol-1-ylmethyl)acetophenone To the suspension of 1-methyl-6-(1H-1,2,4-triazol-1-ylmethyl)phenoxy-1H-benzotriazole (0.5 g) from Example 44 in carbon disulfide (10 ml) were added sequentially acetyl chloride (0.7 ml) and aluminum chloride (0.44 g), for reflux under heating for 8 hours. After addition of water (20 ml), the reaction solution was adjusted to pH 8 with saturated sodium hydrogen carbonate solution, and then the solution was extracted with methylene chloride. The organic layer was washed with saturated sodium chloride solution, and dried over anhydrous sodium sulfate, and then sovent was removed under reduced pressure. The resulting residue was purified by chromatography on a silica gel column(hexane:ethylacetate=1:8), to give the title compound (0.13 g; 23%). The purity of the compound was 98.3% by HPLC.

Example 52

Synthesis of 4-[6-(1-methyl-1H-benzotriazoyloxy)]-3-(1H-1,2,4-triazol-1-ylmethyl)benzonitrile 6-[4-Bromo-2-(1H-1,2,4-triazol-1-ylmethyl)phenoxy]-1-methyl-1H-benzotriazole (2.3 g) from Example 43 was dissolved with anhydrous DMF (20 ml), to which were added palladium acetate (200 mg), triphenylphosphine (0.47 g), KCN (0.6 g) ground in a mortar and calcium hydroxide (62 mg), for stirring under heating at 100° C. for 30 minutes. After the reaction solution was left to stand at room temperature, water was added to the solution prior to extraction twice with methylene chloride. The organic layers were combined together, which was then washed with water (×3), and saturated sodium chloride solution (×1), and then dried over anhydrous sodium sulfate, following to removal of the solvent under reduced pressure. The resulting residue was purified by chromatography on a silica gel column (hexane:ethylacetate=1:6), to recover the title compound (1.8 g; 90%). The purity of the compound was 96.3% by HPLC.

Example 53

Synthesis of 4-[6-(1-methyl-1H-benzotriazoyloxy)]-3-(1H-1,2,4-triazol-1-ylmethyl)benzaldehyde To the suspension of 4-[6-(1-methyl-1H-benzotriazoyloxy)]-3-(1H-1,2,4-triazol-1-ylmethyl)benzonitrile (1.0 g) from Example 52 in THF (20 ml) at −78° C. was added 1.5M DIBAL-H (2.2 ml) for stirring at −78° C. for 2 hours. After the reaction solution was left to stand at room temperature, water (50 ml) was added to the reaction solution, and the solution was extracted with ethylacetate. The organic layers were combined together, which was then washed with water (×3) and saturated sodium chloride solution (×1) and then, dried over anhydrous sodium sulfate, following to removal of the solvent under reduced pressure. The resulting residue was purified by chromatography on a silica gel column (hexane:ethylacetate=1:6), to give the title compound (0.2 g; 21%). The purity of the compound was 92.5% by HPLC.

Example 54

Synthesis of 4-[6-(1-methyl-1H-benzotriazoyloxy)]-3-(1H-1,2,4-triazol-1-ylmethyl)benzoic acid The suspension of 4-[6-(1-methyl-1H-benzotriazoyloxy)]-3-(1H-1,2,4-triazol-1-ylmethyl)benzonitrile (0.5 g) from Example 52 in 1N NaOH (5 ml) and ethanol (5 ml) was refluxed under heating for 8 hours. The reaction solution was concentrated under reduced pressure, followed by addition of water (10 ml) prior to adjustment to pH 4 with acetic acid. The deposited crystal was filtered and washed sequentially in ethanol and ether, to give the title compound (0.48 g; 91%). The purity of the compound was 93.3% by HPLC.

Example 55

Synthesis of 4-[6-(1-methyl-1H-benzotriazoyloxy) ]-3-(1H-1,2,4-triazol-1-ylmethyl)benzoic acid ethyl ester To the suspension of 4-[6-(1-methyl-1H-benzotriazoyloxy)]-3-(1H-1,2,4-triazol-1-ylmethyl)benzoic acid (0.2 g) from Example 54 and potassium carbonate (43 mg) in acetone (5 ml) was added diethyl sulfate (97 mg), for reflux under heating for 6 hours. The reaction solution was concentrated under reduced pressure, followed by addition of water (10 ml), and adjusted to pH 9 with saturated sodium hydrogen carbonate solution and subsequent extraction with methylene chloride. The organic layer was then washed with water and saturated sodium chloride solution, and then, dried over anhydrous sodium sulfate, prior to removal of the solvent under reduced pressure. The resulting residue was purified by chromatography on a silica gel column (methylene chloride:methanol=99:1 to 49:1), to give the title compound (0.14 g; 65%). The purity of the compound was 99.2% by HPLC.

Example 56

Synthesis of 6-[4-ethenyl-2-(1H-1,2,4-benzotriazol-1-ylmethyl)]-1-methyl-1H-benzotriazole To the suspension of methyl bromide triphenylphosphonium bromide (1.07 g) in anhydrous THF (30 ml) was added t-BuOK (0.34 g) at room temperature under stirring for 1 hour. After the reaction mixture was cooled in an ice bath, the solution of 4-[6-(1-methyl-1H-benzotriazoyloxy)]-3-(1H-1,2,4-triazol-1-ylmethyl)benzaldehyde (0.50 g) from Example 53 in methylene chloride (30 ml) was added to the mixture dropwise, and the mixture was stirred at room temperature for 1 hour. The reaction solution was diluted with ethyl acetate (100 ml), and sequentially washed with water and saturated sodium chloride solution. The organic layer was then dried over anhydrous sodium sulfate, and the solvent was removed under reduced pressure. The resulting residue was purified by chromatography on a silica gel column (ethyl acetate:hexane =9:1), to give the title compound (0.47 g; 95%). The purity of the compound was 100% by HPLC.

Example 57

Synthesis of 6-[2-(1H-1,2,4-benzotriazol-1-ylmethyl)-4-(trimethylsilylethynyl)phenoxy]-1-methyl-1H-benzotriazole -1-methyl-1H-benzotriazole (0.50 g) from Example 43, palladium acetate (2.9 mg), triphenylphosphine (6.8 mg), triethylamine (2 ml), and trimethylsilylacetylene (0.29 g) in DMF (5 ml) was stirred under heating at 120° C. for 5 hours. The reaction solution was diluted with methylene chloride (50 ml), and sequentially washed with water and saturated sodium chloride solution. The organic layer was then dried over anhydrous sodium sulfate, and the solvent was removed under reduced pressure. The resulting residue was purified by chromatography on a silica gel column (ethyl acetate:hexane=1:1 to 4:1), to give the title compound (0.39 g; 75%).

Example 58

Synthesis of 6-[4-ethynyl-2-(1H-1,2,4-triazol-1-ylmethyl)phenoxy]-1-methyl-1H-benzotriazole To the solution of 6-[2-(1H-1,2,4-benzotriazol-1-ylmethyl)-4-(trimethylsilylethynyl)phenoxy]-1-methyl-1H-benzotriazole (0.38 g) from Example 57 in methanol (3 ml) was added potassium carbonate (15 mg), for stirring at room temperature for 1.5 hours. The reaction solution was diluted with methylene chloride (30 ml), and sequentially washed with water and saturated sodium chloride solution. The organic layer was then dried over anhydrous sodium sulfate, the solvent was removed under reduced pressure. The resulting crude crystal was washed with hexane to give the title compound (0.25 g; 80%). The purity of the compound was 100% by HPLC.

Example 59

Synthesis of 2-methoxymethoxy-5-(trifluoromethyl)benzaldehyde

To the solution of 4-(trifluoromethyl)phenyl methoxymethyl ether (5 g) in anhydrous ether (50 ml) was gradually added dropwise 1.6M n-BuLi (16.7 ml) at room temperature. After stirring at room temperature for 2 hours, the solution of DMF (4.13 ml) in anhydrous ether (20 ml) was added dropwise over 30 minutes, and the solution was stirred for 1 hour. To the reaction solution was added water, and the ether layer was separated. The ether layer is was washed with water and saturated sodium chloride solution, and dried over anhydrous sodium sulfate, and the solvent was removed under reduced pressure. The resulting residue was purified by chromatography on a silica gel column (methylene chloride:hexane=1:1), to give the title compound (4.49 g; 79%).

Example 60

Synthesis of 2-methoxymethoxy-5-(trifluoromethyl)benzyl alcohol

The solution of 2-methoxymethoxy-5-(trifluoromethyl)benzaldehyde (3.3 g) from Example 59 in anhydrous methanol (20 ml) was cooled in an ice bath, followed by gradual addition of $NaBH_4$ (0.53 g). After stirring at room temperature for 15 minutes, the solvent was removed under reduced pressure. To the residue was added water, and the aqueous layer was extracted with ether. The ether layer was washed with water and saturated sodium chloride solution, and dried over anhydrous sodium sulfate. The solvent was removed under reduced pressure, to give an colorless oil compound as the title compound (3.15 g; 95%).

Example 61

Synthesis of 2-hydroxymethyl-4-(trifluoromethyl)phenol

To the solution of 2-methoxymethoxy-5-(trifluoromethyl)benzyl alcohol (3.15 g) from Example 60 in methanol (20 ml) was added 10% $H_2SO_4$ (5 ml) for reflux under heating for 1 hour. The solvent was removed under reduced pressure. To the residue was added water, the aqueous layer was extracted with ether. The ether layer was washed with water and saturated sodium chloride solution, and dried over anhydrous sodium sulfate. The solvent was removed under reduced pressure, to give the title compound (2.5 g; 98%).

Example 62

Synthesis of 2-(1H-1,2,4-triazol-1-ylmethyl)-4-(trifluoromethyl)phenol

Following Example 21, the title compound was synthesized (1.55 g; 45%) from 2-hydroxymethyl-4-(trifluoromethyl)phenol (2.7 g) from Example 61 and 1H-1,2,4-triazole (1.07 g).

Example 63

Synthesis of N-methyl-2-nitro-5-[2-(1H-1,2,4-triazol-1-ylmethyl)-4-(trifluoromethyl)phenoxy]aniline The solution of 2-(1H-1,2,4-triazol-1-ylmethyl)-4-(trifluoromethyl)phenol (1.0 g) from Example 62, 5-fluoro-N-methyl-2-nitroaniline (700 mg) and $K_2CO_3$ (0.57 g) in DMF (10 ml) was heated at 100° C. for 90 minutes. After the solution was left to stand at room temperature, water was added to the solution, the aqueous layer was extracted with ethyl acetate. The organic layer was washed with saturated sodium chloride solution and dried over anhydrous sodium sulfate. The solvent was removed under reduced pressure, and the residue was purified by chromatography on a silica gel column (methylene chloride:methanol=99:1), to give the title compound (960 mg; 59%).

Example 64

Synthesis of 6-[2-(1H-1,2,4-triazol-1-ylmethyl)-4-(trifluoromethyl)phenoxy]-1-methyl-1H-benzotriazole N-Methyl-2-nitro-5-[2-(1H-1,2,4-triazol-1-ylmethyl)-4-(trifluoromethyl)phenoxy]aniline (1.0 g) from Example 63 was dissolved in acetic acid (10 ml), followed by gradual addition of zinc powder (830 mg) at room temperature. After the addition, ethyl acetate was added to filter off insoluble matetials, and to the filtrate was added saturated sodium hydrogen carbonate solution carefully for separation. The organic layer was washed with saturated sodium chloride solution, and dried over anhydrous sodium sulfate. After removal of the solvent under reduced pressure, 2-methylamino-4-[2-(1H-1,2,4-triazol-1-ylmethyl)- 4-(trifluoromethyl)phenoxy]aniline was obtained as the crude product (920 mg).

The amino compound was dissolved with 10% $H_2SO_4$ (10 ml) under ice cooling, followed by addition of an aqueous solution (1.0 ml) of sodium nitrite (350 mg), and the temperature of the resulting solution was raised up to room temperature for stirring for 5 hours. The solution was neutralized with an aqueous sodium hydrogen carbonate, and the solution was extracted twice with methylene chloride. The organic phase was dried over anhydrous sodium sulfate, and the solvent was distilled off under reduced pressure. The resulting residue was purified by chromatography on a silica gel column (methylene chloride:methanol= 99:1 to 98:2), to give the title compound (790 mg; 83%). The purity of the compound was 99.4% by HPLC.

Example 65

Synthesis of 5-chloro-N-ethyl-2-nitroaniline

Under ice cooling, the solution of N-acetyl-5-chloro-2-nitroaniline (3 g) in THF (30 ml) was added dropwise to the suspension of $LiAlH_4$ (0.53 g) in THF (50 ml) over 30 minutes. The mixture was stirred under ice cooling for 1 hour. Into the resulting reaction solution was added ice with caution, followed by addition of ethyl acetate and saturated sodium chloride solution, and then insoluble materials was filtered off. The ethyl acetate layer was separated, washed with water and saturated sodium chloride solution, and dried over anhydrous sodium sulfate. After removal of the solvent, the residue was purified by chromatography on a silica gel column (hexane:ethyl acetate =19:1), to give the title compound (1.14 g; 41%).

Example 66

Synthesis of 5-[4-chloro-2-(1H-1,2,4-triazol-1-ylmethyl)phenoxy]-N-ethyl-2-nitroaniline At room temperature, NaOMe (0.4 g) was gradually added to the solution of 4-chloro-2-(1H-1,2,4-triazol-1-ylmethyl)phenol (1.4 g) from Example 20 in MeOH (30 ml). After stirring at room temperature for 15 minutes, the mixture was concentrated under reduced pressure for drying. To the resulting product were added DMI (30 ml), 5-chloro-N-ethyl-2-nitroaniline (1.34 g) from Example 65 and copper powder (42 mg) for heating at 130° C. for 3.5 hours. After the resulting mixture was left to stand at room temperature, water and ethyl acetate was added to the mixture, and the copper powder was filtered off. The organic layer was washed with saturated sodium chloride solution, and dried over anhydrous sodium sulfate. After removal of the solvent under reduced pressure, the residue was purified by chromatography on a silica gel column (methylene chloride:methanol=99:1), to give the title compound (1.75 g; 70%).

Example 67

Synthesis of 6-[4-chloro-2-(1H-1,2,4-triazol-1-ylmethyl)phenoxy]-1-ethyl-1H-benzotriazole 5-[4-Chloro-2-(1H-1,2,4-triazol-1-ylmethyl)phenoxy]-N-ethyl-2-aniline (1.7 g) from Example 66 was dissolved in acetic acid (20 ml), followed by gradual addition of zinc powder (1.42 g) at room temperature for stirring for 5 minutes. Ethyl acetate was added to filter off insoluble materials, and the filtrate was concentrated under reduced pressure. To the residue was added saturated sodium hydrogen carbonate solution carefully for making the resulting mixture alkaline, the mixture was extracted with ethyl acetate. The organic layer was washed with saturated sodium chloride solution, and dried over anhydrous sodium sulfate. After removal of the solvent under reduced pressure, a crude product as the residue, i.e. 4-[4-chloro-2-(1H-1,2,4-triazol-1-ylmethyl)phenoxy]-2-ethylaminoaniline was dissolved in 10% $H_2SO_4$ (20 ml) under ice cooling, followed by addition of an aqueous solution (3 ml) of sodium nitrite (0.63 g), and the temperature of the resulting solution was raised up to room temperature for stirring for 1 hour. The solution was neutralized with an aqueous sodium hydrogen carbonate solution, and the solution was extracted twice with methylene chloride. The organic phase was dried over anhydrous sodium sulfate, and the solvent was removed under reduced pressure. The resulting residue was purified by chromatography on a silica gel column (methylene chloride:methanol=99:1 to 49:1), to give the title compound (1.3 g; 81%). The purity of the compound was 99.3% by HPLC.

Example 68

Synthesis of 6-[4-chloro-2-(1H-1,2,4-triazol-1-ylmethyl)phenoxy]-1-methylbenzimidazole To 4-[4-chloro-2-(1H-1,2,4-triazol-1-ylmethyl)phenoxy]-2-methylaminoaniline (100 mg) produced as an intermediate in Example 41 was added formic acid (1 ml), for reflux under stirring for 1 hour. After leaving the solution to stand at room temperature, neutralization with saturated sodium hydrogen carbonate solution was undertaken prior to extraction in methylene chloride. The organic layer was washed with saturated sodium chloride solution, and dried over anhydrous sodium sulfate. After removal of the solvent under reduced pressure, the title compound was generated (95 mg; 92%). The purity of the compound was 97.7% by HPLC.

Example 69

Synthesis of 5-(4-chloro-2-hydroxymethylphenylthio)-N-methyl-2-nitroaniline

The solution of 4-chloro-2-(hydroxymethyl)thiophenol (1.0 g) from Example 16, 5-fluoro-N-methyl-2-nitroaniline (1.0 g) and $K_2CO_3$ (0.81 g) in DMF (20 ml) was heated at 90° C. for 15 minutes. After leaving the solution to stand at room temperature, water was added to the solution prior to extraction in ethyl acetate. The organic layer was washed with saturated sodium chloride solution, and dried over anhydrous sodium sulfate. After removal of the solvent under reduced pressure, the residue was purified by chromatography on a silica gel column (methylene chloride) to give the title compound (1.62 g; 85%).

Example 70

Synthesis of 5-[4-chloro-2-(1H-1,2,4-triazol-1-ylmethyl)phenylthio]-N-methyl-2-nitroaniline To the solution of 5-(4-chloro-2-hydroxymethylphenylthio)-N-methyl-2-nitroaniline (0.20 g) and pyridine (0.055 ml) in methylene chloride (3 ml) was added thionyl chloride (0.049 ml) under ice cooling, for stirring for 15 minutes. Addition of water and extraction with methylene chloride were undertaken, and then, the organic layer was washed with saturated sodium chloride solution, and dried over anhydrous sodium sulfate. After removal of the solvent under reduced pressure, 5-[4-chloro-2-(chloromethyl)phenylthio]-N-methyl-2-nitroaniline (0.21 g) was generated as the crude product. The chloromethyl derivative was dissolved in acetonitrile (3 ml), followed by addition of cesium carbonate (0.3 g) and 1H-1,2,4-triazole (60 mg), and the mixture was refluxed for 15 minutes. After the solution was left to stand at room temperature, the solvent was removed under reduced pressure. To the resulting residue was added water for extraction in methylene chloride. The organic layer was washed sequentially in water and saturated sodium chloride solution, and dried over anhydrous sodium sulfate. After removal of the solvent under reduced pressure, the residue was purified by chromatography on a silica gel column (methylene chloride:methanol=199:1 to 99:1), to give the title compound (140 g; 60%).

Example 71

Synthesis of 6-[4-chloro-2-(1H-1,2,4-triazol-1-ylmethyl)phenylthio]-1-methyl-1H-benzotriazole 5-[4-Chloro-2-(1H-1,2,4-triazol-1-ylmethyl)phenylthio]-N-methyl-2-nitroaniline (0.14 g) from Example 70 was dissolved in acetic acid (2ml), followed by gradual addition of zinc powder (120 mg) at room temperature. After the addition, ethyl acetate was added to filter off insoluble materials, and to the filtrate was added saturated sodium hydrogen carbonate solution carefully for separation. The organic layer was washed with saturated sodium chloride solution, and dried over anhydrous sodium sulfate. After removal of the solvent under reduced pressure, 4-[4-chloro-2-(1H-1,2,4-triazol-1-ylmethyl)phenylthio]-2-methylaminoaniline was obtained as is the crude product.

The aniline derivative was dissolved in 10% $H_2SO_4$ (2 ml) under ice cooling, followed by addition of an aqueous solution (0.5 ml) of sodium nitrite (50 mg), and the temperature of the resulting solution was raised up to room temperature for subsequent stirring for 20 hours. The solution was neutralized with an aqueous sodium hydrogen carbonate solution, and the mixture was extracted twice with methylene chloride. The organic phase was dried over anhydrous sodium sulfate, and the solvent was removed under reduced pressure. The resulting residue was purified by chromatography on a silica gel column (methylene chloride:methanol=99:1 to 98:2), to give the title compound (55 mg; 41%). The purity of the compound was 100 % by HPLC.

Example 72

Synthesis of 2-bromo-5-chlorobenzaldehyde

To the solution of 2-bromo-5-chlorotoluene (25 g) in acetic anhydride (100 ml) and sulfuric acid (20 ml) was added dropwise chromium(VI) oxide (36.5 g) in acetic anhydride (200 ml) for 3 hours at −15° C. The mixture was stirred for 1 hour at −5° C. and then poured into ice-cooled water, and extracted with ether. The organic layer was washed with water and saturated sodium chloride solution, and dried over anhydrous sodium sulfate. After removal of the solvent under reduced pressure, the residue was suspended in ethanol (100 ml) and 3N-HCl (200 ml) and refluxed for 1 hour. After removal of the solvent, water was added to the residue, and extracted with ether.

The organic layer was washed with saturated sodium hydrogencarbonate solution and saturated sodium chloride solution, and dried over anhydrous sodium sulfate. After removal of the solvent under reduced pressure, the residue was purified by chromatography on a silica gel column (hexane:methylene chloride=4:1) to give the title compound (20.5 g; 77%).

Example 73

Synthesis of 2-bromo-5-chlorobenzyl alcohol

2-Bromo-5-chlorobenzaldehyde (20.5 g) from Example 72 was dissolved with dry methanol (200 ml), followed by sodium borohydride (1.06 g) at 0° C., and the mixture was stirred for 30 minutes. After addition of acetone, the solvent was removed under reduced pressure, water was added the obtained residue, and then extracted with ether. The organic layer was washed with saturated sodium hydrogencarbonate solution and saturated sodium chloride solution, and dried over anhydrous sodium sulfate. The solvent was removed under reduced pressure, to give the title compound (19.5 g; 94%)

Example 74

Synthesis of 2-bromo-5-chloro-3-t-butyldimethylsilyloxymethylbenzene

To the solution of 2-bromo-5-chlorobenzylalcohol (10 g) from Example 73 and imidazole (3.23 g) in dry DMF (50ml) was added dropwise t-butyl chloro dimethylsilane in dry DMF (10 ml) for 20 minutes at −0° C. After addition, the mixture was stirred for 30 minutes at room temperature. The mixture was diluted with ether, and washed with saturated sodium chloride solution, dried over anhydrous sodium sulfate.

After removal of the solvent under reduced pressure, the residue was purified by chromatography on a silica gel column (hexane:methylene chloride=4:1) to give the title compound (13.3 g; 88%).

Example 75

Synthesis of α-[2-(t-butyldimethylsilyloxy)methyl-4-chlorophenyl]-1-methyl-1H-benzotriazole-6-methanol To the suspension of magnasium metal (0.84 g) and catalytic amount of iodine in dry ether (3 ml) was added dropwise 2-bromo-5-chloro-3-t-butyldimethylsilyloxymethylbenzene (10.3 g) from Example 74 in dry ether (100 ml) at room temperature, and the mixture was stirred for 1 hour.

The mixture was cooled down to 0° C., a solution of 1-methyl-1H-benzotriazole-6-carboxaldehyde (3.29 g) in THF (100 ml) added dropwise to the mixture for 20 minutes, and then resulting mixture was stirred for 30 minutes at room temperature and cooled down to 0° C., saturated ammonium chloride solution was added and ether layer was separated.

The organic layer was washed with saturated sodium chloride solution, and dried over anhydrous sodium sulfate. After removal of the solvent under reduced pressure, the residue was purified by chromatography on a silica gel column (methylene chloride:ethyl acetate=9:1) to give the title compound (4.31 g; 51%).

Example 76

Synthesis of 6-[2-(t-butyldimethylsilyloxy)methyl-4-chlorobenzyl]-1-methyl-1H-benzotriazole To the solution of α-[2-(t-butyldimethylsilyloxy)methyl-4-chlorophenyl]-1-methyl-1H-benzotriazole-6-methanol (0.5 g) from Example 75 and pyridine (0.11 ml) in methylene chloride (5 ml) was added thionyl chloride (0.1 ml) at 0° C. the mixture was stirred for 30 minutes. The reaction solution was diluted with methylene chloride (5 ml), and sequentially washed with water and saturated sodium chloride solution. The organic layer was dried over anhydrous sodium sulfate, and the solvent was removed under reduced pressure, to give the crude 6-[2-(t-butyldimethyl-silyloxy)methyl-α,4-dichlorobenzyl]-1-methyl-1H-benzotriazole.

The crude α,4-dichloro derivatives in dry DMSO (5 ml) was added sodium borohydride (90 mg), and the mixture was stirred for 2 hours at room temperature, and the additional sodium borohydride (90 mg) was added and stirred for 2.5 days. Ethyl acetate and water was added to the reaction mixture, and the ethyl acetate layer was separated. The organic layer was washed with saturated sodium chloride solution and dried over anhydrous sodium sulfate. After removal of the solvent, the resulting residue was purified by chromatography on a silica gel column (methylene chloride), to give the title compound (0.24 g; 50%).

Example 77

Synthesis of 5-chloro-2-[(1-methyl-1H-bennzotriazole-6-yl)-methyl]benzyl alcohol To the solution of 6-[2-(t-butyldimethylsilyloxy)methyl-4-chlorobenzyl]-1-methyl-1H-benzotriazole (0.24 g) from Example 76 in THF (3 ml) was added 1.0M tetrabutylammonium fluoride(1.2 ml), and stirred for 30 minutes at room temperature. After removal of the solvent, the resulting residue was purified by chromatography on a silica gel column (hexane:ethyl acetate =1:2), to give the title compound (0.16 g; 93%).

Example 78

Synthesis of 6-[4-chloro-2-(chloromethyl)benzyl]-1-methyl-1H-benzotriazole

To the solution of 5-chloro-2-[(1-methyl-1H-benzotriazole-6-yl)methyl]benzyl alcohol (0.16 g) from Example 77 and pyridine (0.05 ml) in methylene chloride (2 ml) was added thionyl chloride (0.04 ml) at 0° C., the mixture was stirred for 30 minutes. After removal of the solvent, the resulting residue was purified by chromatography on a silica gel column (methylene chloride:methanol=199:1), to give the title compound (0.12 g; 70%).

Example 79

Synthesis of 6-[4-chloro-2-(1H-1,2,4-triazol-1-ylmethyl)benzyl]-1-methyl-1H-benzotriazole A suspension of 6-[4-chloro-2-(chloromethyl)benzyl]-1-methyl-1H-benzotriazole (0.11 g) from Example 78, 1H-1,2,4-triazole (37 mg) and cesium carbonate (0.18 g) in acetonitrile (2 ml) was refluxed for 30 minutes. After removal of the solvent, the resulting residue was purified by chromatography on a silica gel column (methylene chloride:methanol=99:1), to give the title compound (63mg; 52%). The purity of the compound was 96.7% by HPLC.

Example 80

Synthesis of 4-[(1-methyl-1H-benzotriazole-6-yl)methyl]-3-(1H-1,2,4-triazol-1-ylmethyl)benzonitrile To the solution of 6-[4-chloro-2-(1H-1,2,4-triazol-1-ylmethyl)benzyl]-1-methyl-1H-benzotriazole (80 mg) from Example 79 and KCN (46 mg) in absolute EtOH (8 ml) was added tetrakis (triphenylphosphine) nickel (0.39 g), heated in a sealed tube for 10 hours at 90°–100° C.

Ethyl acetate was added to filtrate off the insoluble materials, and the filtrate was concentrated under reduced pressure. The resulting residue was purified by chromatography on a silica gel column (ethyl acetate), to give the crude compound. The crude compound was triturated with ether and recrystallized from ethyl acetate to give the title compound (23 mg; 29%). The purity of the compound was 96.5% by HPLC.

Table 10 shows analytical data of the compounds of Examples 1 to 80; and Table 11 shows the structural formulas.

TABLE 10

| Ex. | IR (cm$^{-1}$) | NMR (ppm) (*: 90MHz, non-mark: 270MHz) | mp (°C.) |
|---|---|---|---|
| 1 | neat: 1576, 1477, 1460, 1389, 1259, 1236, 1178, 1120, 870, 770 | CDCl$_3$*: 8.34–8.10(1H, m), 7.98–7.68(1H, m), 7.68–7.35(4H, m), 7.35–7.00(2H, m), 6.90–6.54 (2H, m), 2.27(3H, s) | oil |
| 2 | KBr: 1630, 1597, 1483, 1460, 1252, 1232, 1207, 1182, 1161, 1115 | CDCl$_3$: 7.84–7.79(2H, m), 7.65(1H, d, J=9Hz), 7.47–7.35(2H, m), 7.29–7.14(3H, m), 7.08(1H, d, J=2Hz), 6.90(1H, d, J=9Hz), 2.24(3H, s) | 39.0–40.3 |
| 3 | neat: 1481, 1390, 1261, 1242, 1186, 770 | CDCl$_3$*: 8.34–6.84(9H, m), 6.66(1H, d, J=9Hz), 4.63(2H, s) | oil |
| 5 | neat: 1506, 1479, 1390, 1259, 1240, 1074, 791, 773 | CDCl$_3$: 7.98–7.89(2H, m), 7.69–7.64(2H, m), 7.59–7.47(2H, m), 7.42–7.36(1H, m), 7.21–7.16 (2H, m), 7.11(1H, s), 7.01(1H, d, J=1Hz), 6.83 (1H, dd, J=8, 1Hz), 6.71(1H, d, J=9Hz), 5.25 (2H, s) | oil |
| 6 | neat: 1632, 1506, 1481, 1464, 1250, 1234, 1173, 1159, 1120, 1111 | CDCl$_3$: 7.89–7.83(2H, m), 7.72(1H, d, J=8Hz), 7.59(1H, s), 7.50–7.44(2H, m), 7.26–7.22(2H, m), 7.18(1H, dd, J=9, 2Hz), 7.11–6.98(3H, m), 6.86 (1H, d, J=8Hz), 5.19(2H, s) | oil |
| 7 | neat: 1504, 1481, 1390, 1259, 1240, 1182, 1014, 773, 677 | CDCl$_3$: 8.15(1H, s), 7.99(1H, s), 7.96–7.89(2H, m), 7.68(1H, d, J=8Hz), 7.59–7.48(2H, m), 7.40–7.34(2H, m), 7.21(1H, dd, J=9, 2Hz), 6.81(1H, d, J=8Hz), 6.70(1H, d, J=9Hz), 5.48(2H, s) | oil |
| 8 | KBr: 3298, 1734, | CDCl$_3$*: 11.47(1H, brs), 8.82(1H, d, J=2Hz), | 75.4–76.8 |

TABLE 10-continued

| Ex. | IR (cm$^{-1}$) | NMR (ppm) (*: 90MHz, non-mark: 270MHz) | mp (°C.) |
|---|---|---|---|
| | 1593, 1498, 1257 | 8.28(1H, d, J=9Hz), 7.34(1H, dd, J=9, 2Hz) | |
| 9 | KBr: 1703, 1529, 1338, 1275, 1211, 1144 | CDCl$_3$*: 8.22–7.98(1H, m), 7.68–7.32(2H, m), 3.63–3.46(3H×⅓, m), 3.38(3H×⅔, s) | 89.2–91.6 |
| 10 | KBr: 3383, 1618, 1566, 1498, 1340, 1315, 1261, 1225 | CDCl$_3$*: 8.5–7.7(1H, br), 8.11(1H, d, J=9Hz), 6.82 (1H, d, J=2Hz), 6.61(1H, dd, J=9, 2Hz), 3.01 (3H, d, J=5Hz) | 107.1–108.3 |
| 11 | KBr: 3446, 3151, 1431, 1408, 1269, 1126, 1011, 1001, 820 | CDCl$_3$*: 7.44–7.08(3H, m), 6.77(1H, d, J=8Hz), 4.83(2H, s), 2.5–1.7(1H, br) | 105.6–107.6 |
| 12 | KBr: 3433, 1435, 1410, 1267, 1124, 1003, 822 | DMSO-d$_6$: 9.65(1H, s), 7.26(1H, d, J=3Hz), 7.06 (1H, dd, J=9, 3Hz), 6.76(1H, d, J=9Hz), 5.11 (1H, t, 5Hz), 4.44(2H, d, J=5Hz) | 93.8–97.9 |
| 13 | KBr: 3435, 1427, 1267, 1128, 997, 818 | CDCl$_3$*: 7.58–7.35(3H, m), 6.67(1H, d, J=8Hz), 4.83(2H, brs), 2.7–1.8(1H, br) | 139.6–142.2 |
| 14 | KBr: 3435, 1512, 1452, 1196, 1009, 883, 820 | CDCl$_3$*: 7.38–6.66(4H, m), 4.81(2H, s), 2.9–1.8 (1H, br) | 70.5–75.4 |
| 15 | KBr: 3371, 1610, 1581, 1491, 1458, 1323, 1223, 1009, 908 | CDCl$_3$*: 7.54(1H, brs), 7.05–6.69(3H, m), 4.84 (2H, brs), 2.5–2.1(1H, br) | 131.9–134.0 |
| 16 | KBr: 3290, 2576, 1462, 1402, 1101, 1066, 1036, 808 | CDCl$_3$: 7.39(1H, d, J=2Hz), 7.26(1H, d, J=8Hz), 7.15(1H, dd, J=8, 2Hz), 4.70(2H, s), 3.62(1H, s), 2.2–1.8(1H, br) | 57.3–63.2 |
| 17 | KBr: 3437, 1437, 1230, 1209, 1039, 1009, 999, 820 | CDCl$_3$*: 6.96(1H, s), 6.77–6.48(3H, m), 4.77 (2H, s), 3.73(3H, s), 3.0–2.2(1H, br) | 75.8–76.7 |
| 18 | KBr: 1518, 1281, 1255, 1217, 1201, 1173, 1149, 1001 | CDCl$_3$*: 7.44(1H, brs), 7.14–6.66(3H, m), 4.85 (2H, s), 2.7–2.0(1H, br) | 82.2–84.4 |
| 19 | KBr: 1512, 1427, 1277, 1238, 1111, 1082 | DMSO-d$_6$*: 10.13(1H, s), 7.66(1H, s), 7.26–6.60 (5H, m), 5.06(2H, s) | 164.9–165.6 |
| 20 | KBr: 1500, 1431, 1286, 1273, 1144 | DMSO-d$_6$*: 10.12(1H, s), 8.53(1H, s), 7.94(1H, s), 7.19(1H, dd, J=9, 2Hz), 7.04(1H, d, J=2Hz), 6.84(1H, d, J=9Hz), 5.30(2H, s) | 188.5–191.2 |
| 21 | KBr: 1601, 1514, 1458, 1275, 1250, 1130, 770 | DMSO-d$_6$*: 9.79(1H, s), 8.48(1H, s), 7.92(1H, s), 7.24–6.67(4H, m), 5.30(2H, s) | 146.5–148.5 |
| 22 | KBr: 1497, 1433, 1286, 1144, 816 | DMSO-d$_6$*: 10.14(1H, s), 8.52(1H, s), 7.94(1H, s), 7.30(1H, dd, J=8, 2Hz), 7.16(1H, d, J=2Hz), 6.79(1H, d, J=8Hz), 5.29(2H, s) | 183.3–184.6 |
| 23 | KBr: 1512, 1454, 1441, 1282, 1136, 818 | DMSO-d$_6$: 9.85(1H, s), 8.54(1H, s), 7.96(1H, s), 7.03–6.95(1H, m), 6.85–6.80(2H, m), 5.30(2H, s) | 183.4–184.5 |
| 24 | KBr: 1514, 1425, 1275, 1126, 820 | DMSO-d$_6$*: 10.12(1H, s), 8.51(1H, s), 7.93(1H, s), 7.44(1H, dd, J=8, 2Hz), 7.32(1H, d, J=2Hz), 6.67(1H, d, J=8Hz), 5.27(2H, s) | 176.8–178.6 |
| 25 | KBr: 1516, 1458, 1435, 1425, 1277, 1223, 1201, 1130, 1039, 820 | DMSO-d$_6$*: 9.34(1H, s), 8.48(1H, s), 7.94(1H, s), 6.90–6.42(3H, m), 5.28(2H, s), 3.63(3H, s) | 162.5–165.1 |
| 26 | KBr: 1518, 1452, 1269, 1252, 1213, 1201 | CDCl$_3$*: 8.27(1H, s), 7.99(1H, s), 7.14–6.78 (3H, m), 5.31(2H, s) | 134.2–136.3 |
| 27 | KBr: 1599, 1514, 1425, 1265, 1134, 906, 837 | DMSO-d$_6$*: 10.35(1H, s), 8.50(1H, s), 7.93(1H, s), 7.06(1H, d, J=9Hz), 6.90–6.60(2H, m), 5.29 (2H, s) | 219.6–221.1 |
| 28 | KBr: 1632, 1570, 1510, 1483, 1255, 1211, 1188, 1159 | CDCl$_3$: 8.26–8.14(1H, brs), 8.17(1H, d, J=9Hz), 7.56(1H, s), 7.34(1H, dd, J=9, 2Hz), 7.15(1H, d, J=2Hz), 7.09(1H, s), 6.99(1H, d, J=9Hz), 6.93 (1H, s), 6.19(1H, d, J=2Hz), 6.14(1H, dd, J=9, 2Hz), 5.10(2H, s), 2.92(3H, d, J=5Hz) | oil |
| 29 | KBr: 1632, 1568, 1506, 1477, 1448, 1273, 1221, 1184 | DMSO-d$_6$*: 8.52(1H, s), 8.40–8.16(1H, m), 8.07 (1H, d, J=9Hz), 7.92(1H, s), 7.56–7.32(2H, m), 7.23–6.96(1H, m), 6.27–6.00(2H, m), 5.41(2H, s), 2.83(3H, d, J=5Hz) | 122.0–123.3 |
| 30 | KBr: 1624, 1579, 1572, 1506, 1481, 1261, 1232, 1194 | CDCl$_3$*: 8.24–7.86(4H, m), 7.60–7.38(2H, m), 6.90 (1H, d, J=9Hz), 6.24–6.00(2H, m), 5.33(2H, s), 2.90(3H, d, J=5Hz) | 145.1–147.9 |
| 31 | KBr: 3354, 1628, 1564, 1506, 1444, 1346, 1273, 1225, | CDCl$_3$: 8.19(1H, brs), 8.16(1H, d, J=9Hz), 8.05 (1H, s), 7.91(1H, s), 7.44–7.38(2H, m), 7.30–7.24(1H, m), 7.06–7.03(1H, m), 6.17(1H, d, | 147.1–149.5 |

TABLE 10-continued

| Ex. | IR (cm$^{-1}$) | NMR (ppm)<br>(*: 90MHz, non-mark: 270MHz) | mp<br>(°C.) |
|---|---|---|---|
| | 1159, 1140 | J=2Hz), 6.14(1H, dd, J=9, 2Hz), 5.37(2H, s), 2.89 (3H, d, J=5Hz) | |
| 32 | KBr: 3361, 1632, 1566, 1497, 1444, 1346, 1275, 1257, 1215, 1203, 1138 | CDCl$_3$: 8.3–8.1(1H, br), 8.16(1H, d, J=10Hz), 8.10 (1H, brs), 7.94(1H, brs), 7.15–7.01(3H, m), 6.14– 6.10(2H, m), 5.33(2H, s), 2.89(3H, d, J=5Hz) | 109.9–113.1 |
| 33 | KBr: 1622, 1579, 1568, 1504, 1346, 1261, 1232, 1211, 1194 | CDCl$_3$: 8.3–8.1(2H, br), 8.16(1H, d, 10Hz), 7.95 (1H, brs), 7.71–7.68(2H, m), 6.78(1H, d, J=9Hz), 6.19(1H, d, J=2Hz), 6.13(1H, dd, J=10, 2Hz), 5.33(2H, s), 2.91(3H, d, J=3Hz) | 191.8–193.4 |
| 34 | KBr: 3373, 1626, 1566, 1506, 1500, 1493, 1344, 1273, 1255, 1221, 1140 | CDCl$_3$: 8.3–8.1(2H, br), 8.15(1H, d, J=10Hz), 8.1–7.9(1H, br), 7.00(1H, d, J=8Hz), 6.94–6.87 (2H, m), 6.13–6.10(2H, m), 5.31(2H, s), 3.82(3H, s), 2.88(3H, d, J=5Hz) | 155.7–158.1 |
| 35 | KBr: 1635, 1568, 1500, 1257, 1227, 1203, 1171, 1151, 1140 | CDCl$_3$: 8.2–8.1(1H, br), 8.18(1H, d, J=9Hz), 8.11 (1H, brs), 7.95(1H, brs), 7.25–7.19(2H, m), 7.04 (1H, d, J=9Hz), 6.22(1H, d, J=2Hz), 6.14(1H, dd, J=9, 2Hz), 5.38(2H, s), 2.92(3H, d, J=5Hz) | 168.4–170.6 |
| 36 | KBr: 1632, 1568, 1504, 1444, 1348, 1261, 1230 | CDCl$_3$: 8.3–8.0(2H, br), 8.19(1H, d, J=9Hz), 7.94 (1H, brs), 7.33(1H, d, J=8Hz), 7.23(1H, dd, J=8, 2Hz), 7.01(1H, d, J=2Hz), 6.22(1H, d, J=2Hz), 6.14(1H, dd, J=9, 2Hz), 5.35(2H, s), 2.93(3H, d, J=5Hz) | 130.7–131.9 |
| 37 | KBr: 3458, 1630, 1566, 1493, 1477, 1246, 1230, 1186 | DMSO-d$_6$: 8.7–8.4(1H, br), 8.1–7.9(1H, br), 7.99 (1H, d, J=10Hz), 7.54–7.45(4H, m), 7.18(1H, d, J=9Hz), 6.25–6.21(2H, m), 5.38(2H, s) | 262.5–273.5 (dec.) |
| 38 | KBr: 1504, 1481, 1458, 1234, 1203, 1184, 1117, 852 | CDCl$_3$: 8.03(1H, d, J=9Hz), 7.58(1H, s), 7.29(1H, dd, J=9, 3Hz), 7.19(1H, d, J=3Hz), 7.08–7.03 (2H, m), 6.95(1H, s), 6.87–6.83(2H, m), 5.18(2H, s), 4.21(3H, s) | 175.5–176.0 |
| 39 | KBr: 3383, 3327, 3278, 3219, 1632, 1512, 1485, 1240, 1184 | CDCl$_3$: 8.16(1H, s), 7.96(1H, s), 7.27(1H, d, J=3Hz), 7.18(1H, dd, J=9, 3Hz), 6.72(1H, d, J=9Hz), 6.66(1H, d, J=8Hz), 6.31(1H, d, J=2Hz), 6.27(1H, dd, J=8, 2Hz), 5.39(2H, s) | 127.8–131.2 |
| 40 | KBr: 1512, 1479, 1471, 1271, 1252, 1238, 1173, 1144, 1128, 997, 872 | CD$_3$OD: 8.46(1H, s), 7.92–7.89(2H, m), 7.44 (1H, d, J=3Hz), 7.37(1H, dd, J=9, 3Hz), 7.17–7.11(2H, m), 6.93(1H, d, J=9Hz), 5.51(2H, s) | 227.6–229.9 (dec.) |
| 41 | KBr: 1506, 1485, 1462, 1275, 1238, 1209, 1186 | CDCl$_3$: 8.14(1H, s), 8.03(1H, dd, J=9, 1Hz), 7.95 (1H, s), 7.36(1H, d, J=2Hz), 7.31(1H, dd, J=9, 2Hz), 7.05(1H, dd, J=9, 2Hz), 6.87–6.83(2H, m), 5.42(2H, s), 4.21(3H, s) | 191.2–192.8 |
| 42 | KBr: 1506, 1483, 1275, 1244, 1188, 1142, 1011, 825 | CDCl$_3$: 8.15(1H, s), 7.96(1H, s), 7.54–7.50(2H, m), 7.33(1H, d, J=3Hz), 7.26(1H, dd, J=9, 3Hz), 7.13(1H, dd, J=9, 2Hz), 6.76(1H, d, J=9Hz), 5.44(2H, s), 4.32(3H, s) | 145.2–148.7 |
| 43 | KBr: 1504, 1483, 1462, 1277, 1236, 1207, 1182, 1119 | CDCl$_3$: 8.13(1H, s), 8.03(1H, d, J=9Hz), 7.95(1H, s), 7.50(1H, d, J=2Hz), 7.45(1H, dd, J=9, 2Hz), 7.05(1H, dd, J=9, 2Hz), 6.86(1H, d, J=2Hz), 6.78(1H, d, J=9Hz), 5.41(2H, s), 4.21(3H, s) | 203.1–204.3 |
| 44 | KBr: 1624, 1495, 1468, 1273, 1236, 1203, 1014, 760 | CDCl$_3$: 8.11(1H, s), 8.02(1H, d, J=9Hz), 7.93(1H, s), 7.42–7.32(2H, m), 7.24–7.19(1H, m), 7.07(1H, dd, J=9, 2Hz), 6.91(1H, d, J=8Hz), 6.84(1H, d, J=2Hz), 5.45(2H, s), 4.19(3H, s) | 116.7–117.5 |
| 45 | KBr: 3103, 1504, 1489, 1464, 1273, 1217, 1205, 1138, 1016 | CDCl$_3$: 8.11(1H, s), 8.02(1H, d, J=9Hz), 7.95(1H, s), 7.10–7.03(3H, m), 6.96–6.90(1H, m), 6.78(1H, d, J=2Hz), 5.40(2H, s), 4.19(3H, s) | 142.4–145.7 |
| 46 | KBr: 1504, 1481, 1460, 1234, 1207, 1182, 1119 | CDCl$_3$: 8.17(1H, s), 8.03(1H, d, J=9Hz), 7.96(1H, s), 7.70(1H, d, J=2Hz), 7.63(1H, dd, J=9, 2Hz), 7.04(1H, dd, J=9, 2Hz), 6.88(1H, d, J=2Hz), 6.64(1H, d, J=9Hz), 5.40(2H, s), 4.21(3H, s) | 206.7–208.4 |
| 47 | KBr: 1504, 1493, 1468, 1435, 1273, 1213, 1190, 1014 | CDCl$_3$: 8.05(1H, s), 7.99(1H, dd, J=9, 1Hz), 7.90 (1H, s), 7.06(1H, dd, J=9, 2Hz), 6.98–6.90(3H, m), 6.69(1H, d, J=2Hz), 5.35(2H, s), 4.16(3H, s), 3.82(3H, s) | 180.9–183.1 |
| 48 | KBr: 1506, 1493, 1460, 1273, 1246, 1223, 1198 | CDCl$_3$: 8.25(1H, s), 8.05(1H, d, J=9Hz), 7.99(1H, s), 7.27–7.18(2H, m), 7.06(1H, dd, J=9, 2Hz), 6.93–6.88(2H, m), 5.47(2H, s), 4.23(3H, s) | 177.6–178.0 |
| 49 | KBr: 1502, 1487, 1464, 1408, 1271, 1230, 1205, 1016 | CDCl$_3$: 8.12(1H, s), 8.06(1H, dd, J=9, 1Hz), 7.94 (1H, s), 7.33(1H, d, J=8Hz), 7.17(1H, dd, J=8, 2Hz), 7.05(1H, dd, J=9, 2Hz), 6.92(1H, dd, J=2, 1Hz), 6.83(1H, d, J=2Hz), 5.43(2H, s), 4.23 (3H, s) | 151.4–152.4 |
| 50 | KBr: 1589, 1524, 1508, 1487, 1344, | CDCl$_3$: 8.30(1H, d, J=3Hz), 8.25(1H, s), 8.17(1H, dd, J=9, 3Hz), 8.12(1H, d, J=9Hz), 8.01(1H, s), | 201.5–202.7 |

TABLE 10-continued

| Ex. | IR (cm$^{-1}$) | NMR (ppm) (*: 90MHz, non-mark: 270MHz) | mp (°C.) |
|---|---|---|---|
|  | 1244, 1207, 1093 | 7.10–7.04(2H, m), 6.83(1H, d, J=9Hz), 5.58(2H, s), 4.27(3H, s) |  |
| 51 | KBr: 1682, 1672, 1603, 1491, 1254, 1238, 1205 | CDCl$_3$: 8.20(1H, s), 8.07(1H, dd, J=9, 1Hz), 8.04 (1H, d, J=2Hz), 7.97(1H, s), 7.91(1H, dd, J=9, 2Hz), 7.06(1 H, dd, J=9, 2Hz), 7.01(1H, dd, J=2, 1Hz), 6.84(1H, d, J=9Hz), 5.54(2H, s), 4.24 (3H, s), 2.59(3H, s) | 166.1–168.7 |
| 52 | KBr: 2233, 1606, 1506, 1493, 1460, 1248, 1223, 1207, 833 | CDCl$_3$: 8.24(1H, s), 8.11(1H, dd, J=8, 2Hz), 8.01 (1H, s), 7.65(1H, d, J=2Hz), 7.58(1H, dd, J=9, 2Hz), 7.07–7.03(2H, m), 6.82(1H, d, J=9Hz), 5.53 (2H, s), 4.26(3H, s) | 192.7–194.4 |
| 53 | KBr: 3109, 1693, 1601, 1593, 1491, 1244, 1221, 1209, 1138, 1113 | CDCl$_3$: 9.95(1H, s), 8.22(1H, s), 8.10(1H, dd, J=7, 2Hz), 7.99(1H, s), 7.92(1H, d, J=2Hz), 7.83 (1H, dd, J=8, 2Hz), 7.09–7.06(2H, m), 6.89(1H, d, J=8Hz), 5.58(2H, s), 4.26(3H, s) | 196.0–196.7 |
| 54 | KBr: 1699, 1606, 1516, 1493, 1462, 1306, 1288, 1244, 1200, 1188, 1126 | DMSO-d$_6$: 8.63(1H, s), 8.09(1H, d, J=9Hz), 8.00 (1H, s), 7.91–7.88(2H, m), 7.49,(1H, d, J=2Hz), 7.11(1H, dd, J=9, 2Hz), 6.92(1H, d, J=9Hz), 5.59(2H, s), 4.24(3H, s) | 235.0–236.4 |
| 55 | KBr: 1705, 1610, 1487, 1292, 1250, 1238, 1201, 1180, 1138, 1016 | CDCl$_3$: 8.18(1H, s), 8.13(1H, d, J=2Hz), 8.07(1H, d, J=9Hz), 8.00(1H, dd, J=9, 2Hz), 7.96(1H, s), 7.05(1H, dd, J=9, 2Hz), 6.98(1H, d, J=2Hz), 6.83(1H, d, J=9Hz), 5.52(2H, s), 4.38(2H, q, J=7Hz), 4.23(3H, s), 1.39(3H, t, J=7Hz) | 205.7–206.5 |
| 56 | KBr: 1626, 1506, 1497, 1460, 1273, 1244, 1219, 1209, 1120, 1014, 960, 837 | CDCl$_3$: 8.10(1H, s), 8.02(1H, d, J=9Hz), 7.93(1H, s), 7.42(1H, d, J=2Hz), 7.39(1H, dd, J=8, 2Hz), 7.07(1H, dd, J=9, 2Hz), 6.87(1H, d, J=8Hz), 6.84(1H, d, J=2Hz), 6.69(1H, dd, J=18, 11Hz), 5.71(1H, d, J=18Hz), 5.43(2H, s), 5.28(1H, d, J=11Hz), 4.19(3H, s) | 174.1–176.6 |
| 57 | KBr: 2152, 1504, 1491, 1462, 1250, 1221, 1201, 866, 845 | CDCl$_3$: 8.11(1H, s), 8.03(1H, d, J=9Hz), 7.93(1H, s), 7.49(1H, d, J=2Hz), 7.42(1H, dd, J=9, 2Hz), 7.05(1H, dd, J=9, 2Hz), 6.86(1H, d, J=2Hz), 6.79(1H, d, J=9Hz), 5.41(2H, s), 4.20(3H, s), 0.24(9H, s) | 155.0–155.7 |
| 58 | KBr: 1626, 1506, 1493, 1464, 1275, 1246, 1225, 1211, 1142, 1014, 868, 677 | CDCl$_3$: 8.13(1H, s), 8.05(1H, d, J=9Hz), 7.95(1H, s), 7.51(1H, d, J=2Hz), 7.45(1H, dd, J=8, 2Hz), 7.06(1H, dd, J=9, 2Hz), 6.91(1H, d, J=2Hz), 6.81(1H, d, J=8Hz), 5.44(2H, s), 4.22(3H, s), 3.09(1H, s) | 177.0–179.3 |
| 59 |  | CDCl$_3$: 10.51(1H, s), 8.13(1H, d, J=2Hz), 7.78 (1H, dd, J=9, 2Hz), 7.36(1H, d, J=9Hz), 5.37 (2H, s), 3.55(3H, s) | oil |
| 60 |  | CDCl$_3$: 7.64(1H, d, J=2Hz), 7.52(1H, dd, J=9, 2Hz), 7.18(1H, d, J=9Hz), 5.28(2H, s), 4.75 (2H, s), 3.49(3H, s) | oil |
| 61 | KBr: 1624, 1333, 1284, 1200, 1180, 1161, 1124, 1115, 1072 | CDCl$_3$: 7.85(1H, s), 7.47(1H, dd, J=8, 2Hz), 7.37–7.31(1H, m), 7.00–6.95(1H, m), 4.94(2H, d, J=5Hz), 2.36(1H, t, J=5Hz) | 81.5–85.0 |
| 62 | KBr: 1624, 1516, 1344, 1325, 1161, 1140, 1120, 1074, 677 | DMSO-d$_6$: 10.9–10.7(1H, br), 8.58(1H, s), 7.96 (1H, s), 7.53(1H, dd, J=8, 2Hz), 7.39(1H, d, J=2Hz), 7.00(1H, d, J=8Hz), 5.39(2H, s) | 186.4–188.4 |
| 63 | KBr: 1630, 1618, 1576, 1508, 1327, 1240, 1234, 1165, 1117 | CDCl$_3$: 8.3–8.1(1H, br), 8.20(1H, d, J=9Hz), 8.13 (1H, s), 7.95(1H, s), 7.65–7.62(2H, m), 7.08 (1H, d, J=9Hz), 6.28(1H, d, J=2Hz), 6.17(1H, dd, J=9, 2Hz), 5.45(2H, s), 2.94(3H, d, J=5Hz) | 132.8–134.7 |
| 64 | KBr: 1500, 1331, 1254, 1242, 1209, 1182, 1169, 1142, 1120, 1115, 1074 | CDCl$_3$: 8.19(1H, s), 8.08(1H, d, J=9Hz), 7.97(1H, s), 7.65(1H, s), 7.57(1H, d, J=9Hz), 7.06(1H, dd, J=9, 2Hz), 6.99(1H, d, J=2Hz), 6.89(1H, d, J=9Hz), 5.53(2H, s), 4.24(3H, s) | 209.4–211.0 |
| 65 | KBr: 3369, 1618, 1566, 1493, 1408, 1387, 1336, 1309, 1259, 1221 | CDCl$_3$*: 8.5–7.6(1H, br), 8.11(1H, d, J=9Hz), 6.82 (1H, d, J=2Hz), 6.59(1H, dd, J=9, 2Hz), 3.33 (2H, dq, J=7, 5Hz), 1.38(3H, t, J=7Hz) | 86.3–89.1 |
| 66 | KBr: 3373, 1630, 1572, 1504, 1342, 1317, 1271, 1259, 1236, 1223 | CDCl$_3$: 8.2–8.0(2H, br), 8.17(1H, d, J=9Hz), 7.95 (1H, brs), 7.38–7.34(2H, m), 6.97(1H, dd, J=7, 2Hz), 6.17(1H, d, J=2Hz), 6.12(1H, dd, J=9, 2Hz), 5.34(2H, s), 3.24–3.14(2H, m), 1.33(3H, t, J=7Hz) | 133.2–134.4 |
| 67 | KBr: 1620, 1504, 1483, 1460, 1238, 1201, 1115, 862 | CDCl$_3$: 8.12(1H, s), 8.03(1H, d, J=9Hz), 7.94(1H, s), 7.35(1H, d, J=3Hz), 7.30(1H, dd, J=9, 3Hz), 7.03(1H, dd, J=9, 2Hz), 6.88(1H, d, J=2Hz), 6.84(1H, d, J=9Hz), 5.41(2H, s), 4.58(2H, q, J=7Hz), 1.59(3H, t, J=7Hz) | 137.9–140.7 |

TABLE 10-continued

| Ex. | IR (cm⁻¹) | NMR (ppm) (*: 90MHz, non-mark: 270MHz) | mp (°C.) |
|---|---|---|---|
| 68 | KBr: 1504, 1475, 1460, 1240, 1184, 1119 | CDCl$_3$: 8.18(1H, s), 7.97(1H, s), 7.90(1H, s), 7.78 (1H, d, J=9Hz), 7.33(1H, d, J=2Hz), 7.22(1H, dd, J=9, 2Hz), 6.95(1H, dd, J=9, 2Hz), 6.89(1H, d, J=2Hz), 6.72(1H, d, J=9Hz), 5.45(2H, s), 3.79 (3H, s) | 157.3–158.5 |
| 69 | KBr: 3377, 1608, 1568, 1323, 1263, 1217 | CDCl$_3$: 8.2–8.0(1H, br), 8.01(1H, d, J=9Hz), 7.68 (1H, d, J=2Hz), 7.50(1H, d, J=8Hz), 7.35(1H, dd, J=8, 2Hz), 6.41(1H, d, J=2Hz), 6.20(1H, dd, J=9, 2Hz), 4.76(2H, d, J=6Hz), 2.87(3H, d, J=5Hz), 1.98(1H, t, J=6Hz) | 102.1–104.4 |
| 70 | KBr: 3338, 1614, 1564, 1491, 1344, 1319, 1207, 1138 | CDCl$_3$: 8.2–8.0(1H, br), 8.07(1H, s), 8.03(1H, d, J=9Hz), 7.94(1H, s), 7.57(1H, d, J=8Hz), 7.42 (1H, dd, J=8, 2Hz), 7.31(1H, d, J=2Hz), 6.33 (1H, d, J=2Hz), 6.16(1H, dd, J=9, 2Hz), 5.47 (2H, s), 2.86(3H, d, J=5Hz) | 151.2–153.4 |
| 71 | KBr: 1506, 1201, 1144, 1103, 1016, 820, 679 | CDCl$_3$: 8.10(1H, s), 7.98–7.95(2H, m), 7.40(1H, d, J=8Hz), 7.34(1H, dd, J=8, 2Hz), 7.25(1H, d, J=2Hz), 7.21–7.13(2H, m), 5.50(2H, s), 4.22 (3Hz, s) | 164.9–166.8 |
| 72 | KBr: 1693, 1672, 1456, 1248, 1190, 1093, 1032, 897, 818 | CDCl$_3$*: 10.30(1H, s), 7.88(1H, d, J=3Hz), 7.61 (1H, d, J=9Hz), 7.41(1H, dd, J=9, 3Hz) | 64.3–67.1 |
| 73 | KBr: 3232, 1456, 1439, 1099, 1063, 1022, 810 | CDCl$_3$*: 7.50(1H, d, J=3Hz), 7.46(1H, d, J=8Hz), 7.13(1H, dd, J=8, 3Hz), 4.72(2H, d, J=6Hz), 1.97(1H, t, J=6Hz) | 82.0–85.7 |
| 74 | neat: 2954, 2929, 1255, 1120, 1105, 1088, 1026, 839 | CDCl$_3$: 7.53(1H, d, J=3Hz), 7.41(1H, d, J=9Hz), 7.10(1H, dd, J=9, 3Hz), 4.68(2H, s), 0.97(9H, s), 0.14(6H, s) | oil |
| 75 | KBr: 3232, 2951, 2927, 2854, 1255, 1207, 1122, 1095, 1076, 1047 | CDCl$_3$: 7.95(1H, d), 7.78(1H, s), 7.32(1H, d), 7.24(1H, dd), 7.15(1H, d), 7.06(1H, d), 6.19(1H, d), 4.79(1H, d), 4.50(1H, d), 4.31(3H, s), 4.14 (1H, d), 0.91(9H, s), 0.13(3H, s), 0.10(3H, s) | 159.3–162.9 |
| 76 | KBr: 2951, 2927, 2856, 1458, 1257, 1198, 1097, 1074 | CDCl$_3$: 7.96(1H, d), 7.48(1H, d), 7.21(1H, dd), 7.19(1H, d), 7.11(1H, s), 7.02(1H, d), 4.61(2H, s), 4.22(3H, s), 4.13(2H, s), 0.88(9H, s), 0.02 (6H, s) | 99.3–102.5 |
| 77 | KBr: 3292, 1479, 1444, 1207, 1093, 1051, 1022 | CDCl$_3$: 7.94(1H, d), 7.48(1H, d), 7.26(1H, dd), 7.18(1H, d), 7.15(1H, s), 7.10(1H, d), 4.64(2H, d), 4.22(3H, s), 4.21(2H, s), 1.75(1H, t) | 138.4–139.4 |
| 78 | KBr: 1489, 1458, 1273, 1203, 1198, 1176, 1113, 1012 | CDCl$_3$: 7.98(1H, d), 7.41(1H, d), 7.29(1H, dd), 7.20(1H, d), 7.18(1H, s), 7.09(1H, d), 4.49(2H, s), 4.30(2H, s), 4.24(3H, s) | 130.0–132.1 |
| 79 | KBr: 1508, 1273, 1203, 1144, 1018, 893, 810, 777, 681 | CDCl$_3$: 7.98(1H, d), 7.95(1H, s), 7.92(1H, s), 7.35 (1H, dd), 7.19–7.13(3H, m), 7.08(1H, s), 5.25 (2H, s), 4.23(3H, s), 4.21(2H, s) | 155.9–157.5 |
| 80 | KBr: 3433, 2231, 1626, 1610, 1508, 1275, 1207, 1136 | CDCl$_3$: 8.02(1H, d), 7.99(1H, s), 7.98(1H, s), 7.65 (1H, dd), 7.42(1H, d), 7.33(1H, d), 7.13(1H, dd), 7.11(1H, d), 5.33(2H, s), 4.32(2H, s), 4.25 (3H, s) | 191.4–194.1 |

TABLE 11

| Example | |
|---|---|
| 1 | |
| 2 | |

TABLE 11-continued
| Example | |
|---|---|
| 3 | 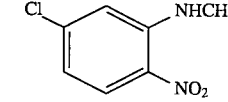 |
| 4 | 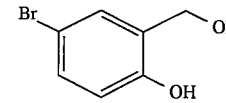 |
| 5 | 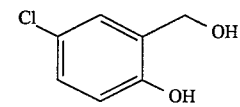 |
| 6 | 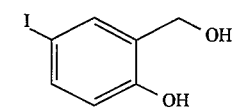 |
| 7 | 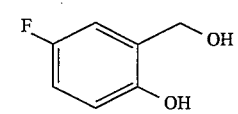 |
| 8 | 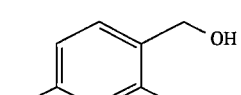 |
| 9 | 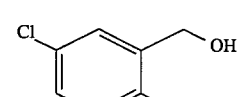 |
TABLE 11-continued
| Example | |
|---|---|
| 10 | 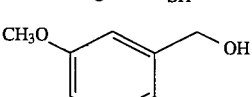 |
| 11 | 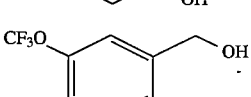 |
| 12 | 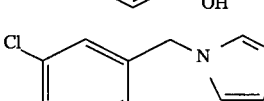 |
| 13 | 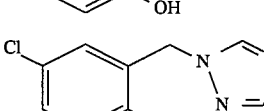 |
| 14 | 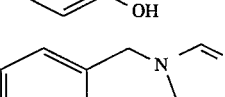 |
| 15 | 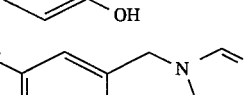 |
| 16 | 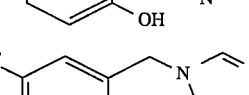 |
| 17 | |
| 18 | |
| 19 | |
| 20 | |
| 21 | |
| 22 | |
| 23 | |

TABLE 11-continued

| Example | |
|---|---|
| 24 | 4-iodo-2-(1,2,4-triazol-1-ylmethyl)phenol |
| 25 | 4-methoxy-2-(1,2,4-triazol-1-ylmethyl)phenol |
| 26 | 4-trifluoromethoxy-2-(1,2,4-triazol-1-ylmethyl)phenol |
| 27 | 4-chloro-2-(1,2,4-triazol-1-ylmethyl)phenol |
| 28 | 2-[4-chloro-2-(imidazol-1-ylmethyl)phenoxy]-5-(methylamino)-4-nitrobenzene |
| 29 | 2-[4-chloro-2-(1,2,4-triazol-1-ylmethyl)phenoxy]-5-(methylamino)-4-nitrobenzene |
| 30 | 2-[4-bromo-2-(1,2,4-triazol-1-ylmethyl)phenoxy]-5-(methylamino)-4-nitrobenzene |
| 31 | 2-[2-(1,2,4-triazol-1-ylmethyl)phenoxy]-5-(methylamino)-4-nitrobenzene |
| 32 | 2-[4-fluoro-2-(1,2,4-triazol-1-ylmethyl)phenoxy]-5-(methylamino)-4-nitrobenzene |
| 33 | 2-[4-iodo-2-(1,2,4-triazol-1-ylmethyl)phenoxy]-5-(methylamino)-4-nitrobenzene |
| 34 | 2-[4-methoxy-2-(1,2,4-triazol-1-ylmethyl)phenoxy]-5-(methylamino)-4-nitrobenzene |
| 35 | 2-[4-trifluoromethoxy-2-(1,2,4-triazol-1-ylmethyl)phenoxy]-5-(methylamino)-4-nitrobenzene |
| 36 | 2-[5-chloro-2-(1,2,4-triazol-1-ylmethyl)phenoxy]-5-(methylamino)-4-nitrobenzene |
| 37 | 2-[4-chloro-2-(1,2,4-triazol-1-ylmethyl)phenoxy]-5-amino-4-nitrobenzene |

TABLE 11-continued
| Example | |
|---|---|
| 38 | 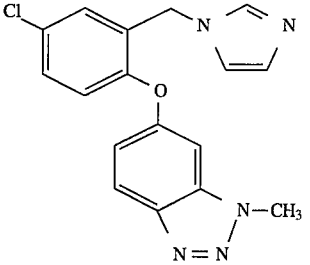 |
| 39 | 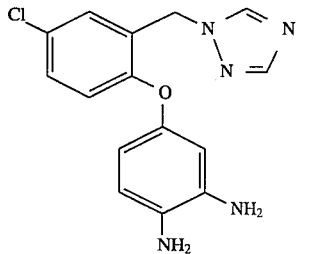 |
| 40 | 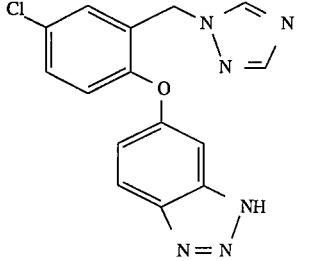 |
| 41 | 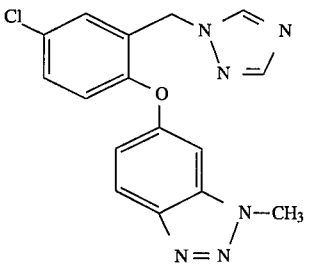 |
| 42 | 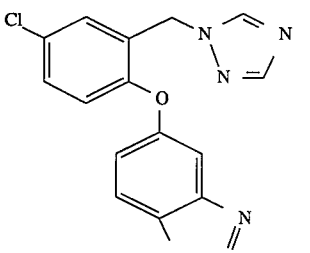 |
| 43 | 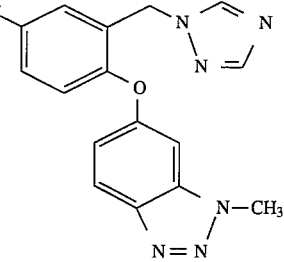 |
| 44 | 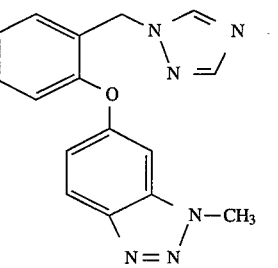 |
| 45 | 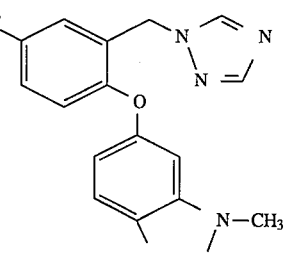 |
| 46 | 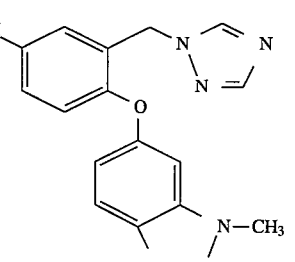 |
| 47 | 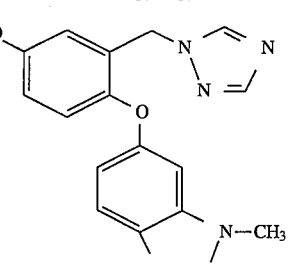 |
| 48 | 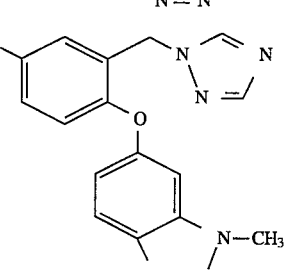 |

TABLE 11-continued
| Example | |
|---|---|
| 49 | 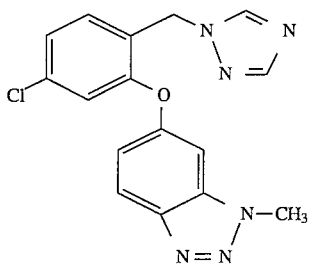 |
| 50 | 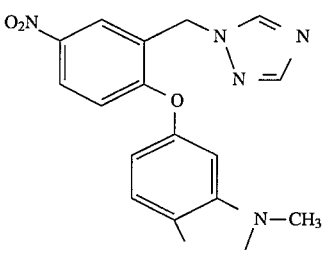 |
| 51 | 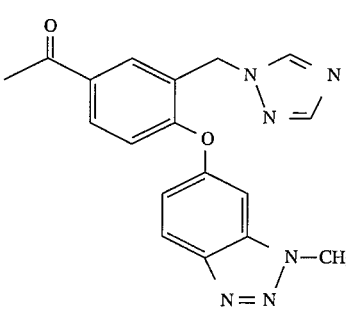 |
| 52 | 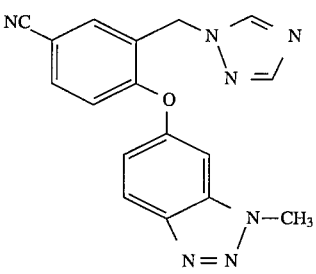 |
| 53 | 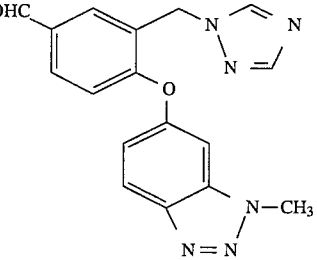 |
| 54 | 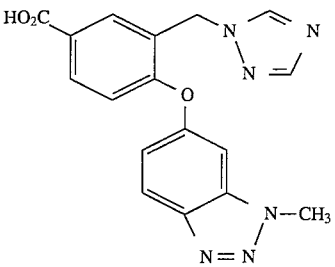 |
| 55 | 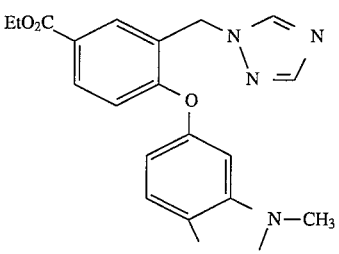<br>Et = $C_2H_5$ |
| 56 | 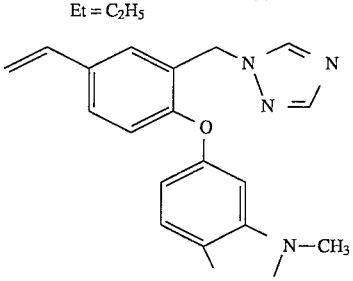 |
| 57 | 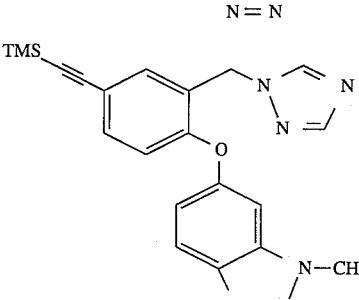<br>TMS = $Si(CH_3)_3$ |
| 58 | 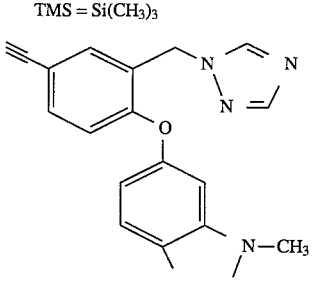 |
| 59 | 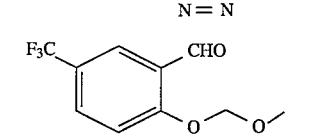 |

TABLE 11-continued

| Example | Structure |
|---|---|
| 60 | 5-(trifluoromethyl)-2-(methoxymethoxy)benzyl alcohol: F₃C-substituted benzene with CH₂OH and OCH₂OCH₃ groups |
| 61 | 5-(trifluoromethyl)-2-hydroxybenzyl alcohol: F₃C-substituted benzene with CH₂OH and OH groups |
| 62 | F₃C-substituted benzene with CH₂-(1,2,4-triazol-1-yl) and OH |
| 63 | F₃C-benzene with CH₂-triazole and O-linked to (3-NHCH₃, 4-NO₂)-phenyl |
| 64 | F₃C-benzene with CH₂-triazole and O-linked to phenyl bearing N(CH₃)–N=N (methyltriazene) |
| 65 | 5-chloro-2-nitro-N-ethylaniline: Cl-benzene with NHC₂H₅ and NO₂ |
| 66 | Cl-benzene with CH₂-triazole and O-linked to phenyl bearing NHC₂H₅ and NO₂ |
| 67 | Cl-benzene with CH₂-triazole and O-linked to phenyl bearing N(C₂H₅)–N=N triazene |
| 68 | Cl-benzene with CH₂-triazole and O-linked to phenyl bearing N(CH₃) triazene |
| 69 | Cl-benzene with CH₂OH and S-linked to (3-NHCH₃, 4-NO₂)-phenyl |
| 70 | Cl-benzene with CH₂-triazole and S-linked to (NHCH₃, NO₂)-phenyl |
| 71 | Cl-benzene with CH₂-triazole and S-linked to phenyl bearing N(CH₃)–N=N triazene |
| 72 | 5-chloro-2-bromobenzaldehyde (CHO, Cl, Br on benzene) |
| 73 | 5-chloro-2-bromobenzyl alcohol (CH₂OH, Cl, Br on benzene) |
| 74 | 5-chloro-2-bromobenzyl OTBS ether (CH₂OTBS, Cl, Br on benzene) |

TABLE 11-continued

| Example | |
|---|---|
| 75 | 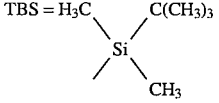 |
| 76 | |
| 77 | |
| 78 | |
| 79 | |
| 80 | |

Examples of pharmaceutical preparations containing the compounds in accordance with the present invention will now be described hereinbelow, but are not intend to limit this invention.

Example 1 of Pharmaceutical Preparation

| Tablets | |
|---|---|
| Compound of Example 41 | 2 g |
| Polyethylene glycol 6000 | 100 g |
| Sodium lauryl sulfate | 15 g |
| Corn starch | 30 g |
| Lactose | 348 g |
| Magnesium stearate | 5 g |

The components described above are individually weighed. Then, polyethylene glycol 6000 is heated to 70° to 80° C., followed by addition of the compound of Example 41, sodium lauryl sulfate, corn starch, and lactose, and then they are mixed together. The resulting mixture is left to stand for cooling. The solidified mixture is charged into a grinding machine for preparing granules. The granules are mixed with magnesium stearate, and then they are compressed and tableted to prepare tablets, each of 250 mg in weight.

Example 2 of Pharmaceutical Preparation

| Capsules | |
|---|---|
| Compound of Example 43 | 10 g |
| Lactose | 340 g |
| Corn starch | 50 g |
| Microcrystalline cellulose | 95 g |
| Magnesium stearate | 5 g |

The components described above are individually weighed. Then, the four components except magnesium stearate are mixed to be homogeneous. After addition of magnesium stearate, they are mixed additionally for another several minutes. For preparation of capsules, the mixture is filled in an appropriate hard capsule at 250 mg/capsule in weight, using a capsule filling device.

Example 3 of Pharmaceutical Preparation

| Injections | |
|---|---|
| Compound of Example 52 | 1 g |
| Propylene glycol | 200 g |
| Sterile distilled water for injections | qs |

The components described above are individually weighed. Then, the compound of Example 52 is dissolved in propylene glycol. Sterile distilled water for injections is added to the resulting solution to a final volume of 1,000 ml, which is then sterilized by filtration and is divided into 10-ml ampules at 5 ml/ampule. The ampules are fused and sealed for preparing injections.

Example 4 of Pharmaceutical Preparation

| Suppositories | |
|---|---|
| Compound of Example 50 | 5 g |
| Polyethylene glycol 1500 | 250 g |
| Polyethylene glycol 4000 | 250 g |

The compound of Example 50 is sufficiently ground in a mortar to prepare microfine powder, which is then prepared into suppositories, each of 1 g, by a fusing method.

Thus, it has been indicated that the azolyl methyl phenyl derivatives in accordance with the present invention exert superior aromatase inhibitory activity in vitro and that the derivatives significantly lower blood estrogen level and have higher specificity for aromatase inhibition in vivo in animal experiments using an experimental rat model, in addition to the finding that the derivatives are highly safe. It has been also demonstrated that the azolyl methyl phenyl derivatives in accordance with the present invention are superior in terms of at least any one of the characteristic properties.

The azolyl methyl phenyl derivatives in accordance with the present invention are extremely useful as the prophylactic agents and/or therapeutical agents for estrogen dependent-diseases, for example, estrogen-dependent cancers (ex. breast cancer, ovarian cancer, endometrium cancer, etc.), endometriosis, uterine leiomyoma, benign breast diseases, mastopathy, premature labor, benign prostatic hyperplasia, prostate cancer, precocious puberty, gynecomastia, male infertility relating to oligospermia and cholelithiasis. Also, the derivatives are useful as contraceptive agents for females.

The compounds of the present invention are useful as aromatase inhibitory agents for use in the form of reagents and in animals, because the compounds have aromatase inhibitory activity in vitro and in vivo.

What is claimed is:

1. A compound represented by the following formula (I):

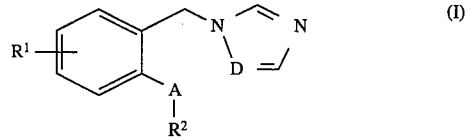

wherein A represents methylene group, oxygen atom or sulfur atom; D represents nitrogen atom $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; $R^2$ represents an atomic group represented by formula (II);

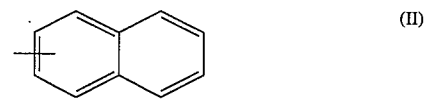

or formula (III);

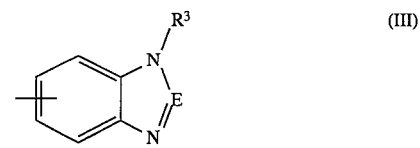

wherein E represents nitrogen atom or methine group; and $R^3$ represents hydrogen atom or $C_1$ to $C_4$ alkyl group linear or branched, or a salt thereof.

2. The compound or a salt thereof according to claim 1, wherein A is oxygen atom; D is nitrogen atom; and the substituting position of $R^1$ is at position 4; and $R^2$ is an atomic group represented by the formula (III) and bound to position 6.

3. The compound or a salt thereof according to claim 1, wherein E is nitrogen atom; and $R^3$ is methyl group.

4. The compound or a salt thereof according to claim 1, wherein $R^1$ is halogen atom, cyano group or nitro group.

5. The compound or a salt thereof according to claim 1, wherein $R^1$ is vinyl group or ethynyl group.

6. A therapeutical composition for estrogen-dependent diseases, comprising an effective amount to treat said estrogen-dependent disease of a compound represented by the following (I):

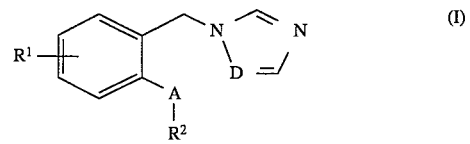

wherein A represents methylene group, oxygen atom or sulfur atom; D represents nitrogen atom; $R^1$ represents halogen atom, cyano group, nitro group, $C_1$ to $C_2$ alkoxy group which may or may not be substituted with one or two or more fluorine atoms, $C_1$ to $C_2$ alkyl group which may or may not be substituted with one or two or more fluorine atoms, $C_2$ to $C_5$ alkenyl group linear or branched, $C_2$ to $C_5$ alkynyl group linear or branched, $C_1$ to $C_2$ alkoxycarbonyl group, carboxyl group, acetyl group, formyl group or hydrogen atom; $R^2$ represents an atomic group represented by formula (II):

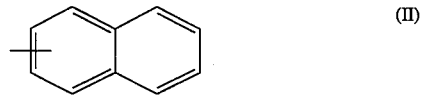

or formula (III):

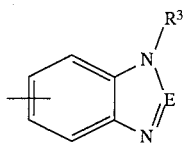

wherein E represents nitrogen atom or methine group; and R$^3$ represents hydrogen atom or C$_1$ to C$_4$ alkyl group linear or branched,
or a pharmaceutically acceptable salt thereof; and a pharmaceutically acceptable carrier thereof.

7. The therapeutic composition for estrogen-dependent diseases according to claim 6, wherein A is oxygen atom; D is nitrogen atom; and the substituting position of R$^1$ is at position 4; and R$^2$ is an atomic group represented by the formula (III) and bound to position 6.

8. The therapeutical composition for estrogen-dependent diseases according to claim 6, wherein E is nitrogen atom; and R$^3$ is methyl group.

9. The therapeutical composition for estrogen-dependent diseases according to claim 6, wherein R$^1$ is halogen atom, cyano group or nitro group.

10. The therapeutical composition for estrogen-dependent diseases according to claim 6, wherein R$^1$ is vinyl group or ethynyl group.

11. The compound or a salt thereof according to claim 2, wherein E is nitrogen atom; and R$^3$ is methyl group.

12. The compound or a salt thereof according to claim 2, wherein R$^1$ is halogen atom, cyano group or nitro group.

13. The compound or a salt thereof according to claim 3, wherein R$^1$ is halogen atom, cyano group or nitro group.

14. The compound or a salt thereof according to claim 11, wherein R$^1$ is halogen atom, cyano group or nitro group.

15. The compound or a salt thereof according to claim 2, wherein R$^1$ is vinyl group or ethynyl group.

16. The compound or a salt thereof according to claim 3, wherein R$^1$ is vinyl group or ethynyl group.

17. The compound or a salt thereof according to claim 11, wherein R$^1$ is vinyl group or ethynyl group.

18. The therapeutical composition for estrogen-dependent diseases according to claim 7, wherein E is nitrogen atom; and R$^3$ is methyl group.

19. The therapeutical composition for estrogen-dependent diseases according to claim 7, wherein R$^1$ is halogen atom, cyano group or nitro group.

20. The therapeutical composition for estrogen-dependent diseases according to claim 8, wherein R$^1$ is halogen atom, cyano group or nitro group.

21. The therapeutical composition for estrogen-dependent diseases according to claim 18, wherein R$^1$ is halogen atom, cyano group or nitro group.

22. The therapeutical composition for estrogen-dependent diseases according to claim 7, wherein R$^1$ is vinyl group or ethynyl group.

23. The therapeutical composition for estrogen-dependent diseases according to claim 8, wherein R$^1$ is vinyl group or ethynyl group.

24. The therapeutical composition for estrogen-dependent diseases according to claim 18, wherein R$^1$ is vinyl group or ethynyl group.

* * * * *